United States Patent
Emig et al.

(10) Patent No.: US 9,587,275 B2
(45) Date of Patent: *Mar. 7, 2017

(54) SINGLE MOLECULE SEQUENCING WITH TWO DISTINCT CHEMISTRY STEPS

(71) Applicant: Pacific Biosciences of California, Inc., Menlo Park, CA (US)

(72) Inventors: Robin Emig, Belmont, CA (US); Lei Jia, Newbury Park, CA (US); Jeremiah Hanes, Menlo Park, CA (US); Lubomir Sebo, Redwood City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,136

(22) Filed: Sep. 8, 2015

(65) Prior Publication Data

US 2016/0010150 A1 Jan. 14, 2016

Related U.S. Application Data

(63) Continuation of application No. 14/072,343, filed on Nov. 5, 2013, which is a continuation of application
(Continued)

(51) Int. Cl.
*C12Q 1/68* (2006.01)
*C07H 19/10* (2006.01)
(Continued)

(52) U.S. Cl.
CPC .......... *C12Q 1/6869* (2013.01); *C07H 19/10* (2013.01); *C07H 19/11* (2013.01); *C07H 19/20* (2013.01);
(Continued)

(58) Field of Classification Search
CPC ............ C12Q 1/6869; C12Q 2521/301; C12Q 2525/186; C12Q 2563/107
(Continued)

(56) References Cited

U.S. PATENT DOCUMENTS 6,001,566 A 12/1999 Canard et al.
6,221,592 B1 4/2001 Schwartz et al.
(Continued)

FOREIGN PATENT DOCUMENTS

EP 1105529 B1 9/2005
WO 96/27025 9/1996
(Continued)

OTHER PUBLICATIONS

Abramova, et al., "A facile and effective synthesis of dinucleotide 50-triphosphates," Bioorganic & Medicinal Chemistry 15 (2007) 6549-6555.
(Continued)

*Primary Examiner* — Jezia Riley
(74) *Attorney, Agent, or Firm* — Robert H. Reamey

(57) ABSTRACT

Methods, Compositions, and Systems are provided for nucleic acid sequencing where the sequential incorporation of nucleotides uses two distinct chemical steps. A plurality of nucleotide analogs, each having a labeled leaving group at its 3' hydroxyl can be sequentially added to a growing strand in the presence of a selective cleaving activity that cleaves the 3' hydroxyl leaving group preferentially after it has been incorporated. The selective cleaving agent can comprise an exonuclease activity, and the exonuclease activity can be a polymerase-associated exonuclease activity. Nucleotide analogs having labels on both a cleavable polyphosphate portion and on a 3' hydroxyl leaving group can provide signals characteristic of nucleotide analog incorporation. Systems having illumination optics, collection optics,
(Continued)

and substrates observe signals from the labels as they are being incorporated into a growing nucleic acid strand, allowing for the sequencing of template nucleic acids.

19 Claims, 13 Drawing Sheets

Related U.S. Application Data

No. 13/022,926, filed on Feb. 8, 2011, now Pat. No. 8,603,741.

(60) Provisional application No. 61/305,856, filed on Feb. 18, 2010.

(51) Int. Cl.
    *C07H 19/11*   (2006.01)
    *C07H 19/20*   (2006.01)
    *C07H 19/213*  (2006.01)

(52) U.S. Cl.
    CPC ......... *C07H 19/213* (2013.01); *C12Q 1/6874* (2013.01); *C12Q 2521/301* (2013.01); *C12Q 2525/186* (2013.01); *C12Q 2563/107* (2013.01)

(58) Field of Classification Search
    USPC ........................................ 435/6.1, 91.1, 6.12
    See application file for complete search history.

(56) References Cited

U.S. PATENT DOCUMENTS

| | | | |
|---|---|---|---|
| 6,255,083 | B1  | 7/2001  | Williams et al. |
| 6,287,821 | B1* | 9/2001  | Shi ........................ C07H 19/10 435/6.12 |
| 6,780,591 | B2  | 8/2004  | Williams et al. |
| 7,270,951 | B1  | 9/2007  | Stemple et al. |
| 7,329,492 | B2  | 2/2008  | Hardin et al. |
| 7,414,116 | B2  | 8/2008  | Milton et al. |
| 2009/0325172 | A1  | 12/2009 | Milton et al. |
| 2010/0255487 | A1* | 10/2010 | Beechem ............... C07H 19/20 435/6.12 |

FOREIGN PATENT DOCUMENTS

| | | |
|---|---|---|
| WO | 99/57321 A1 | 11/1999 |
| WO | 00/53805 A1 | 9/2000 |
| WO | 00/53812    | 9/2000 |
| WO | 01/92284 A1 | 12/2001 |
| WO | 02/29003 A2 | 4/2002 |
| WO | 2008/018839 A1 | 2/2008 |

OTHER PUBLICATIONS

Abramova, et al., "Design and synthesis of dinucleotide 50-triphosphates with expanded functionality," Bioorganic & Medicinal Chemistry 16 (2008) 9127-9132.

Abramova, et al., "Synthesis of morpholine nucleoside triphosphates," Tetrahedron Letters 45 (2004) 4361-4364.

Beese, et al. "Structural basis for the 3' 5' exonuclease activity of *Escherichia coli* DNA polymerase 1: a two metal ion mechanism," The EMBO Journal (1991) vol. 10 No. 1 pp. 25-33.

Bowers, et al., "Virtual terminator nucleotides for next-generation DNA sequencing,"—Supplemental Material, Nature Methods: doi:10.1038/nmeth.1354.

Bowers, et al., "Virtual terminator nucleotides for next-generation DNA sequencing," Nature Methods | vol. 6 No. 8 | Aug. 2009 | 593-597.

Brautigam, "Structural Principles for the Inhibition of the 30-50 Exonuclease Activity of *Escherichia coli* DNA Polymerase I by Phosphorothioates," J. Mol. Biol. (1998) 277, p. 363-377.

Cook, et al., "Nucleoside S-Alkyl Phosphorothioates. 111. Application to Oligonucleotide Synthesis," Journal of the American Chemical Society, 91:23 1 Nov. 5, 1969, p. 6479-6484.

Eid, et al., "Real-Time DNA Sequencing from Single Polymerase Molecules," Science, Jan. 2, 2009/10.1126/ science.1162986.

Finn, et al., "Efficient incorporation of positively charged 2¢, 3¢-dideoxynucleoside-5¢-triphosphates by DNA polymerases and their application in 'direct-load' DNA sequencing," Nucleic Acids Research, 2003, vol. 31, No. 16. 4769-4778.

Foquet, et al. "Improved fabrication of zero-mode waveguides for single-molecule detection," Journal of Applied Physics (2008) 103, 034301.

Hoard, et al., "Conversion of Mono- and Oligodeoxyribonucleotides to 5'-Triphosphates," Journal ofthe American Chemical Society 87.8 Apr. 20, 1965, p. 1785-1788.

Johnson, et al. "Toxicity of Antiviral Nucleoside Analogs and the Human Mitochondrial DNA Polymerase," The Journal of Biological Chemistry (2001) vol. 276, No. 44, Issue of Nov. 2, pp. 40847-40857.

Korlach, et al., "Long, Processive Enzymatic DNA Synthesis Using 100% Dye-Labeled Terminal Phosphate-Linked Nucleotides," Nucleosides, Nucleotides and Nucleic Acids (2008) 27:1072:1083.

Korlach, et al., "Selective aluminum passivation for targeted immobilization of single DNA polymerase molecules in zero-mode waveguide nanostructures," Proceedings of the National Academy of Sciences U.S.A. (2008) 105(4): 1176-1181.

Krutyakov, "Properties of Autonomous 3'→5' Exonucleases," ISSN 0006 2979, Biochemistry (Moscow), 2009, vol. 74, No. 8, pp. 821 823.

Lebedev, et al., "Preparation of Oligodeoxynucleotide 5-Triphosphates Using Solid Support Approach," Nucleosides, Nucleotides & Nucleic Acids, 20(4-7), 1403-1409 (2001).

Levene, et al., "Zero-mode waveguides for single-molecule analysis at high concentration" Science (2003) 299:682-686.

Lundquist, et al., "Parallel confocal detection of single molecules in real time," Optics Letters, vol. 33, Issue 9, pp. 1026-1028.

Meyer, et al. "Differential Removal of Thymidine Nucleotide Analogues from Blocked DNA Chains by Human Immunodeficiency Virus Reverse Transcriptase in the Presence of Physiological Concentrations of 29-oxynucleoside iphosphates," Antimicrobial Agents and Chemotherapy, (2000) 44(12): 3465-3472.

Meyer, et al., "Unblocking of chain-terminated primer by HIV-1 reverse transcriptase through a nucleotide-dependent mechanism," Proc. Natl. Acad. Sci. USA (1998) vol. 95, pp. 13471-13476.

Mitsis, "Exonucleases," Encyclopedia of Life Sciences © 2001, John Wiley & Sons, Ltd. www.els.net.

Perez-Arnaiz, et al., "Functional Importance of Bacteriophage φ29 DNA Polymerase Residue Tyr148 in Primer-terminus Stabilisation at the 3'-5' Exonuclease Active Site," J. Mol. Biol. (2009) 391, 797-807.

Reha-Krantz, "DNA polymerase proofreading: Multiple roles maintain genome stability," Biochim. Biophys. Acta (2009), doi:10. 1016/j.bbapap.2009.06.012.

Shevlev, "The 3'-5' Exonucleases," Nature Reviews Molecular Cell Biology, vol. 3, May 2002, p. 1-12.

Wolfe, et al., "Synthesis and Polymerase Incorporation of 5'-Amino-2',5'-Dideoxy-5'-N-Triphosphate Nucleotides," Nucleic Acids Research (2002) 30(17):3739-47.

Wu, et al., "3-O-modified nucleotides as reversible terminators for pyrosequencing," 16462-16467 PNAS Oct. 16, 2007 vol. 104 No. 42.

Yarbrough, et al. "Stacking Interactions in Fluorescent Nucleotide Analogs Containing 1-Aminonapthalene-5-Sulfonate at the Phosphoryl Terminus", J.Biol. Chem. 255(20), 9907-9911, 1980.

Zhong, et al., "Dinucleotide Analogues as Novel Inhibitors of RNA-Dependent RNA Polymerase of Hepatitis C Virus," Antimicrobial Agents and Chemotherapy, Aug. 2003, p. 2674-2681.

\* cited by examiner

SINGLE MOLECULE SEQUENCING WITH TWO DISTINCT CHEMISTRY STEPS

CROSS-REFERENCE TO RELATED APPLICATIONS

This application is a continuation of U.S. patent application Ser. No. 14/072,343 filed Nov. 5, 2013, which is a continuation of U.S. patent application Ser. No. 13/022,926 filed Feb. 8, 2011, which claims the benefit under 35 U.S.C. §119(e) of U.S. Ser. No. 61/305,856, filed Feb. 18, 2010, which are hereby expressly incorporated by reference in their entirety.

STATEMENT REGARDING FEDERALLY SPONSORED RESEARCH

Not Applicable.

BACKGROUND OF THE INVENTION

Nucleic acid sequences encode the necessary information for living things to function and reproduce, and are essentially a blueprint for life. Determining such sequences is therefore a tool useful in pure research into how and where organisms live, as well as in applied sciences such drug development. In medicine, sequencing tools can be used for diagnosis and to develop treatments for a variety of pathologies, including cancer, heart disease, autoimmune disorders, multiple sclerosis, or obesity. In industry, sequencing can be used to design improved enzymatic processes or synthetic organisms. In biology, such tools can be used to study the health of ecosystems, for example, and thus have a broad range of utility.

An individual's unique DNA sequence provides valuable information concerning their susceptibility to certain diseases. The sequence will provide patients with the opportunity to screen for early detection and to receive preventative treatment. Furthermore, given a patient's individual blueprint, clinicians will be capable of administering personalized therapy to maximize drug efficacy and to minimize the risk of an adverse drug response. Similarly, determining the blueprint of pathogenic organisms can lead to new treatments for infectious diseases and more robust pathogen surveillance. Whole genome DNA sequencing will provide the foundation for modern medicine. Sequencing of a diploid human genome requires determining the sequential order of approximately 6 billion nucleotides. Sequencing of RNA can also provide valuable information relating to which portions of the genome are being expressed by single cells or groups of cells. Greater knowledge of expression can provide keys to understanding and treating many diseases and conditions, including providing a molecular level understanding of the progression of cancer.

A variety of methods have been developed with the goal of providing efficient, cost effective, accurate, and high throughput sequencing. Single-molecule nucleic acid sequencing-by-synthesis is a sequencing method that has the potential to revolutionize the understanding of biological structure and function. While such sequencing methods have been shown to provide reliable sequencing information, further improvements in the quality of sequencing information is desired. For example, in current sequencing-by-synthesis methods, errors in sequencing can occur that lead to incorrect base calling. The present invention provides systems, compositions, and methods of for improving the quality of nucleic acid sequence information.

BRIEF SUMMARY OF THE INVENTION

In some aspects, the invention provides a method for sequencing a nucleic acid template comprising: providing a sequencing mixture comprising a polymerase enzyme, a template nucleic acid, a primer, a polymerase regent solution having the components for carrying out template directed synthesis of a growing nucleic acid strand, a plurality of types of nucleotide analogs; wherein each type of nucleotide analog has a labeled leaving group, each with a different label, that blocks further nucleotide incorporations at the 3' hydroxyl position of the incorporated nucleotide analog; and a selective cleaving activity which more effectively cleaves a leaving group from an incorporated nucleotide analog than from an unincorporated nucleotide analog; carrying out nucleic acid synthesis such that a plurality of nucleotide analogs are added sequentially whereby: i) a nucleotide analog is incorporated, then ii) the labeled leaving group on that nucleotide analog is cleaved by the selective cleaving activity, making the 3' hydroxyl group available for a subsequent nucleotide analog addition; and detecting light from the labels while the polymerase reaction is occurring to determine a sequence of the template nucleic acid.

In some embodiments the selective cleaving activity comprises an enzyme activity. In some embodiments the enzyme activity comprises exonuclease, esterase, or phosphatase activity. In some embodiments the enzyme activity is an activity that cleaves a phosphate, or an ester linkage. In some embodiments the polymerase enzyme comprises the enzyme activity. In some embodiments the enzyme activity comprises an exonuclease activity. In some embodiments the polymerase enzyme comprises the exonuclease activity.

In some embodiments the selective cleaving activity cleaves an incorporated nucleotide analog at a rate that is at least 10 times greater than rate of cleavage of an unincorporated nucleotide analog. In some embodiments the selective cleaving activity cleaves an incorporated nucleotide analog at a rate that is at least 100 times greater than rate of cleavage of an unincorporated nucleotide analog. In some embodiments the selective cleaving activity cleaves an incorporated nucleotide analog at a rate that is at least 1000 times greater than rate of cleavage of an unincorporated nucleotide analog.

In some embodiments wherein the selective cleaving activity selectively cleaves the labeled leaving group while the nucleotide analog is associated with the polymerase enzyme. In some embodiments the labeled leaving group is cleaved while the nucleotide analog is associated with the polymerase enzyme at a rate that is at least 10 times greater than rate of cleavage before the nucleotide analog is incorporated. In some embodiments the labeled leaving group is cleaved while the nucleotide analog is associated with the polymerase enzyme at a rate that is at least 100 times greater than rate of cleavage before the nucleotide analog is incorporated. In some embodiments the labeled leaving group is cleaved while the nucleotide analog is associated with the polymerase enzyme at a rate that is at least 1000 times greater than rate of cleavage before the nucleotide analog is incorporated.

In some embodiments the polymerase enzyme is immobilized on a substrate. In some embodiments multiple single polymerase enzymes are immobilized on the substrate, and sequencing from each polymerase enzyme is monitored concurrently.

In some embodiments the template nucleic acid is immobilized on a substrate. In some embodiments multiple single nucleic acid templates are immobilized on the substrate, and sequencing from each polymerase enzyme is monitored concurrently. In some embodiments the sequencing reaction occurs within an optical confinement on a surface.

In some embodiments the plurality of types nucleotide analogs is four types of nucleotide analogs having bases corresponding to A, G, C, and T, or A, C, G, and U. In some embodiments the template nucleic acid comprises DNA or RNA or a DNA/RNA hybrid. In some embodiments the label comprises a fluorescent label. In some embodiments the fluorescent label comprises a fluorescent dye or a fluorescent particle. In some embodiments the labeled leaving groups are attached to the oxygen at the 3' hydroxyl of the nucleotide analogs.

In some aspects, the invention provides a method for sequencing a nucleic acid template comprising: providing a sequencing mixture comprising a polymerase enzyme, a template nucleic acid, a primer, a polymerase regent solution having the components for carrying out template directed synthesis of a growing nucleic acid strand, a plurality of types of nucleotide analogs; wherein each type of nucleotide analog has attached to its polyphosphate portion a first labeled leaving group comprising a first label, and attached to its 3' hydroxyl a second labeled leaving group comprising a second label; wherein each type of nucleotide analog has at least one different label from each other type of nucleotide analog; and wherein the second labeled leaving group blocks further nucleotide analog additions, and a selective cleaving activity which selectively cleaves a leaving group from an incorporated nucleotide more effectively than cleaving an unincorporated nucleotide analog; carrying out nucleic acid synthesis such that a plurality of nucleotide analogs are added sequentially whereby: i) a nucleotide analog is incorporated, resulting in release of the first labeled leaving group, then ii) the second labeled leaving group on that nucleotide analog is cleaved by the selective cleaving activity, making the 3' hydroxyl group available for a subsequent nucleotide analog addition; and detecting light from the labels while the polymerase reaction is occurring to determine a sequence of the template nucleic acid.

In some aspects, the invention provides the selective cleaving activity comprises an enzyme activity. In some embodiments the invention provides the enzyme activity comprises exonuclease, esterase, or phosphatase activity. In some embodiments the enzyme activity is an activity that cleaves a phosphate, or an ester linkage. In some embodiments the polymerase enzyme comprises the enzyme activity. In some embodiments the enzyme activity comprises an exonuclease activity.

In some embodiments the polymerase enzyme comprises the exonuclease activity.

In some embodiments the selective cleaving activity cleaves the second labeled leaving group from a an incorporated nucleotide analog at a rate that is at least 100 times greater than rate of cleavage from an unincorporated nucleotide analog. In some embodiments the selective cleaving activity selectively cleaves the labeled leaving group while the nucleotide analog is associated with the polymerase enzyme. In some embodiments the labeled leaving group is cleaved while the nucleotide analog is associated with the polymerase enzyme at a rate that is at least 100 times greater than rate of cleavage before the nucleotide analog is incorporated.

In some embodiments the polymerase enzyme is immobilized on a substrate. In some embodiments multiple single polymerase enzymes are immobilized on the substrate, and sequencing from each polymerase enzyme is monitored concurrently.

In some embodiments the template nucleic acid is immobilized on a substrate. In some embodiments multiple single nucleic acid templates are immobilized on the substrate, and sequencing from each polymerase enzyme is monitored concurrently.

In some embodiments the sequencing reaction occurs within an optical confinement on a surface. In some embodiments the plurality of types nucleotide analogs is four types of nucleotide analogs having bases corresponding to A, G, C, and T, or A, C, G, and U. In some embodiments the template nucleic acid comprises DNA or RNA or a DNA/RNA hybrid.

In some embodiments the first label and the second label comprise fluorescent labels. In some embodiments the first label and the second label comprise fluorescent dyes. In some embodiments the first and second labels have substantially independent fluorescence when connected to the nucleotide analog. In some embodiments the first and second labels substantially interact via FRET or quenching when connected to the nucleotide analog.

In some embodiments the sequencing mixture comprises four types of nucleotide analogs, the four types having bases corresponding to A, G, C, and T, or A, C, G, and U, and each of the types of nucleotide analogs has a different first label. In some embodiments the sequencing mixture comprises four types of nucleotide analogs, the four types having bases corresponding to A, G, C, and T, or A, C, G, and U, and each of the types of nucleotide analogs has a different second label. In some embodiments the sequencing mixture comprises four types of nucleotide analogs, the four types having bases corresponding to A, G, C, and T, or A, C, G, and U, and each of the types of nucleotide analogs has a different first label and a different second label, each first label different from each second label.

In some embodiments the second label acts as a FRET donor, and the first label acts as a FRET acceptor. In some embodiments each first label acts as a quencher for each second label.

In some aspects, the invention provides a method for sequencing a nucleic acid template comprising: providing a sequencing mixture comprising a polymerase enzyme, a template nucleic acid, a primer, a polymerase regent solution having the components for carrying out template directed synthesis of a growing nucleic acid strand, a plurality of types of cyclic nucleotide analogs; wherein each type of cyclic nucleotide analog comprises a ring that is formed by a labeled linker K1 and a cleavable group U, the linker attached to the 5' polyphosphate portion of the nucleotide analog and to the cleavable group, and the cleavable group attached to the oxygen of the 3' hydroxyl of the cyclic nucleotide analog, wherein each type of nucleotide analog has a different label from each other type of cyclic nucleotide analog; carrying out nucleic acid synthesis such that a plurality of nucleotide analogs are added sequentially whereby: i) a cyclic nucleotide analog is incorporated into the growing strand, resulting in the opening of the ring between the alpha and beta phosphates of the 5' polyphosphate portion such that the growing strand is attached to the alpha phosphate, and the beta phosphate comprises the end of a chain attached to the oxygen of the 3' hydroxyl, then ii) the end of the chain comprising the beta phosphate reacts with the cleavable group U to cleave a labeled cyclic leaving group and to release the 3' hydroxyl, making the 3' hydroxyl group available for a subsequent cyclic nucleotide analog addition; and detecting light from the labels while the polymerase reaction is occurring to determine a sequence of the template nucleic acid.

In some embodiments the alpha and beta phosphates are connected with a moiety R1 which remains connected to the beta phosphate on cleavage, and which reacts with the cleavable group U. In some embodiments the moiety R1 comprises a nucleophile. In some embodiments R1 comprises an oxygen, sulfur, nitrogen or carbon nucleophile. In some embodiments the polymerase enzyme is immobilized on a substrate.

In some embodiments multiple single polymerase enzymes are immobilized on the substrate, and sequencing from each polymerase enzyme is monitored concurrently. In some embodiments the template nucleic acid is immobilized on a substrate.

In some embodiments multiple single nucleic acid templates are immobilized on the substrate, and sequencing from each polymerase enzyme is monitored concurrently. In some embodiments the sequencing reaction occurs within an optical confinement on a surface.

In some embodiments the plurality of types nucleotide analogs is four types of nucleotide analogs having bases corresponding to A, G, C, and T, or A, C, G, and U.

In some aspects, the invention provides a system for sequencing a nucleic acid template comprising: providing a sequencing mixture comprising a polymerase enzyme, a template nucleic acid, a primer, a polymerase regent solution having the components for carrying out template directed synthesis of a growing nucleic acid strand, a plurality of types of nucleotide analogs; wherein each type of nucleotide analog has a labeled leaving group, each with a different label, that blocks further nucleotide incorporations at the 3' hydroxyl position of the incorporated nucleotide analog; and a selective cleaving activity which more effectively cleaves a leaving group from an incorporated nucleotide analog than from an unincorporated nucleotide analog; a substrate onto which either the template nucleic acid or the polymerase enzyme is bound; an excitation light source directed to the portions on the substrate where the template nucleotide or polymerase enzyme is bound; a detector for detecting emitted light from the labeled leaving groups while the polymerase reaction is occurring; and a computer to determine a sequence of the template nucleic acid using the detected light from the labeled leaving groups.

In some embodiments the selective cleaving activity comprises an enzyme activity. In some embodiments the enzyme activity comprises exonuclease, esterase, or phosphatase activity. In some embodiments the enzyme activity is an activity that cleaves a phosphate, or an ester linkage. In some embodiments the polymerase enzyme comprises the enzyme activity. In some embodiments the enzyme activity comprises an exonuclease activity. In some embodiments the polymerase enzyme comprises the exonuclease activity.

In some embodiments each nucleotide analog further comprise a second fluorescently labeled leaving group comprising a second fluorescent label attached to its phosphate portion, such that the label is released when the nucleotide analog is incorporated into the a growing strand. In some embodiments a plurality of single template nucleic acids or single polymerase enzymes is bound to the substrate and the system is capable independently detecting emitted light from sequencing reactions involving them.

In some aspects, the invention provides novel compositions.

DETAILED DESCRIPTION OF THE INVENTION

General

Figures 1A, 1B:
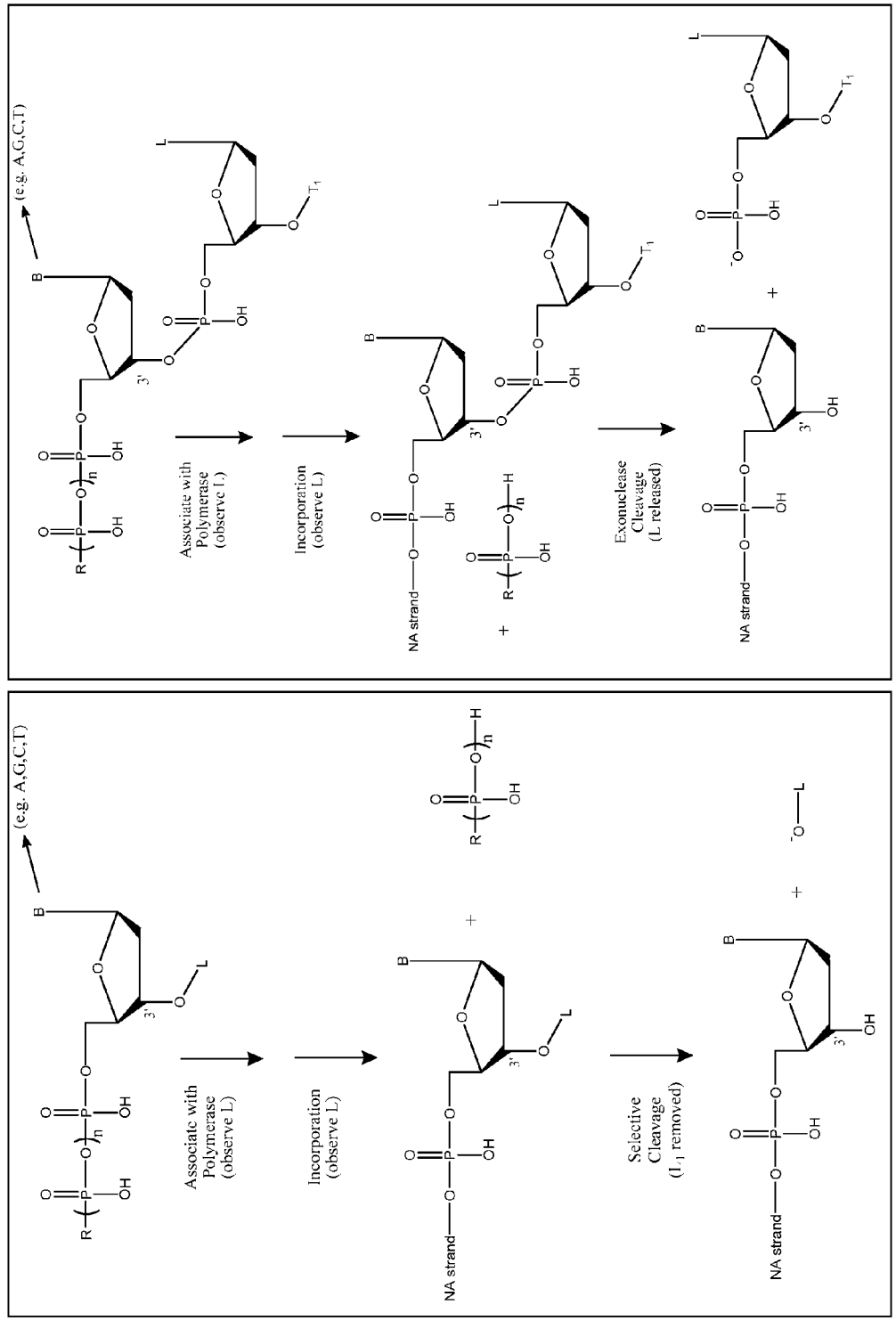
FIG. 1A shows an embodiment of a single molecule sequencing method of the invention which is performed using the signal from a labeled 3' hydroxyl leaving group which is cleaved by a selective cleaving activity.
FIG. 1B shows an embodiment of a single molecule sequencing method of the invention in which an exonuclease acts as the selective cleaving agent to cleave a monophosphate nucleoside 3' hydroxyl leaving group.

In some aspects, the invention provides methods, compositions, and systems for carrying out nucleic acid sequencing, and in particular single molecule nucleic acid sequencing. Methods of sequencing have been recently developed in which a the incorporation of nucleotides into a growing strand during template dependent nucleic acid synthesis by a polymerase enzyme can be observed, providing information on the sequence of the template nucleic acid molecule. One such method is described, for example, in Eid et al., Science, 323, 133-138. The methods of the invention provide improved approaches to sequencing which overcome some potential sources of error in these methods.

For example, some single molecule sequencing methods involve observing a labeled nucleotide analog while it is in the active site of the enzyme. The nucleotide analog which is incorporated can show different signal characteristics than diffusing or unincorporated nucleotides, for example by having a longer retention time in the polymerase enzyme. Where the nucleotide analog has a labeled leaving group that is released upon incorporation, the incorporated nucleotide will be associated with the enzyme from nucleotide binding, to cleavage and release of the pyrophosphate (or polyphosphate) portion of the nucleotide. The observation of a characteristic peak indicates that a nucleotide has been incorporated, and where each type of nucleotide analog has a different label, the observed signals can be used to put together the sequence of the template nucleic acid by sequentially identifying each incorporated nucleotide. These types of approaches can be used for the rapid and accurate sequencing of a nucleic acid template. However, in a small number of cases, a nucleotide analog which is not incorporated will spend enough time associated with the enzyme that it can be incorrectly identified as an incorporated nucleotide. This can occur, for example, for a cognate nucleotide analog that fails to become incorporated, and is released (referred to as branching), or it can occur for a non-cognate nucleotide analog which spends a longer time associated with the enzyme than is typical (referred to as non-cognate extra). In either case, these events can result in errors in the determination of the sequence of the template nucleic acid. Even though these events may occur relatively rarely, they can still present a problem, as there is a desire to have a sequencing accuracy that is as high as possible.

In some prior methods, a label on a terminal phosphate of a nucleotide analog which is cleaved and released upon incorporation is used to observe the nucleotide analog while it is associated with the enzyme. In the methods of the present invention, an incorporated nucleotide analog remains observable past the time when the pyrophosphate is released, allowing for a longer time period for observation, and for a more distinct signal or set of signals indicative of incorporation. The methods of the invention allow for higher accuracy sequencing, for example by further differentiating the observed signal from an incorporation event from a signal from the observed signal from a branching or non-cognate extra event.

For the sequencing methods of the current invention, two distinct chemical steps, for example two chemical cleavage steps, are required before a label is released. In some embodiments of the invention, nucleotide analogs are utilized which are reversibly blocked at their 3' hydroxyl group with a labeled leaving group, preventing extension from the incorporated nucleotide until the labeled leaving group is removed. The sequencing reaction mixture, which contains the nucleotide analogs, also contains a selective cleaving activity which cleaves the 3' hydroxyl leaving group after it has been incorporated, but will not effectively to cleave the 3' hydroxyl leaving group of the nucleotide analog before it has been incorporated. Thus, as the labeled 3' hydroxy leaving group remains until after it is removed by the selective cleaving activity, the label generally remains observable for a longer period of time than if the label was cleaved by the action of the polymerase.

It is important to distinguish the current method from previously described "flush and scan" type methods, which in some cases can also include a blocked 3' hydroxyl group. See, e.g. U.S. Pat. No. 7,270,951. In such systems, labeled, 3' hydroxyl blocked nucleotide analogs are added to an immobilized enzyme/template and allowed to react. The excess nucleotide analogs are then washed away from the bound enzyme/template, and the sample is scanned to determine which nucleotide analog has been added. After scanning, in a separate step, the 3' hydroxyl blocking groups are removed (photochemically or chemically), and the process is repeated.

Unlike these "flush and scan" type methods, for the present methods, a selective cleaving activity is present in the sequencing reaction mixture during a time period over which multiple nucleotide analogs are incorporated. This selective cleaving activity allows for the polymerase reaction to proceed without the need for flushing out the unincorporated nucleotides after each incorporation step. In the current method, the user is not required to take steps to chemically or photochemically remove the blocking group between incorporation steps.

The selective cleaving activity can be, for example, an enzymatic activity. In some embodiments, the selective cleaving activity comprises a template dependent 3'-5' exonuclease activity. The template-dependent exonuclease activity can be selected such that the cleavage of the 3' hydroxyl leaving group will readily occur after a nucleotide analog has been incorporated and is part of a double-stranded nucleic acid, but where very little or substantially no cleavage of the 3' hydroxyl leaving group will occur for the unincorporated nucleotides in solution. In some cases, the exonuclease activity will be associated with the polymerase enzyme that incorporates the nucleotide. A number of naturally occurring polymerase enzymes have a 3'-5' exonuclease proofreading activity. This exonuclease activity can be modified, reduced, or eliminated by well known methods of enzyme engineering, for example by replacing one or more amino acids in the enzyme with a different amino acid. Where the exonuclease activity is part of the polymerase enzyme, the exonuclease activity will generally be near the nucleotide which has just been incorporated, poised to remove the 3' hydroxyl leaving group.

In some aspects, the invention utilizes nucleotide analogs having two labeled leaving groups, each of which is cleaved in a separate chemical step. As used herein, the term chemical step generally refers to a step involving the formation and/or breakage of a chemical bond. A chemical step can be carried out by an enzyme. Exemplary nucleotide analogs have one leaving group which is removed upon incorporation of the nucleotide analog into a growing nucleic acid strand, and another leaving group which is attached to the 3' hydroxyl group on the sugar moiety of the nucleotide analog, blocking further nucleotide analog incorporation until the leaving group is removed. The use of nucleotide analogs having two separate labeled leaving groups, each cleaved at a different chemical step provides for an improved ability to correctly identify which base has been incorporated into the growing nucleic acid strand. The two labels can be independent labels which have little or substantially no interaction with one another, thus acting as separate labels. In some embodiments the two labels interact with one another, for example by Fluorescence Resonance Energy Transfer (FRET) or quenching. The interaction between the two labels can provide information about the proximity of the two labels within the system in a manner that allows for improved identification of which nucleotide analog has been incorporated.

The observation of the incorporation of labeled nucleotides can be carried out in a manner that minimizes the background, for example from unincorporated nucleotides which are present in solution. In some cases, the reactions are carried out in an optical confinement such as a zero mode waveguide (ZMW). The polymerase enzyme or the nucleic acid template can be immobilized within the optical confinement such that the reaction can be observed as it proceeds within the optical confinement. The polymerase enzyme or the nucleic acid template are generally immobilized or bound to a substrate so that multiple nucleotide analog additions can be optically followed. It is generally desirable to have multiple polymerase reactions, each independently observed occurring simultaneously.

FIG. 1A shows an exemplary embodiment of a method of the invention. A plurality of nucleotide analogs having a labeled leaving group L on their 3' hydroxyl groups is provided as part of a sequencing reaction mixture comprising a polymerase enzyme, a template nucleic acid, a primer, a selective cleaving agent, and the components necessary for carrying out nucleic acid additions to a growing nucleic acid strand complementary to the template. For this example, four nucleotide analogs, each corresponding to A, G, T, and C are included in the mixture. Each of the four nucleotide analogs has a different, independently observable label, for example a fluorescent dye label. This example shows NTP analogs having a deoxy ribose sugar which will produce DNA when polymerized into a growing strand. Nucleotides having other sugar components, such as ribose to produce RNA, or other non-natural sugars which will produce a non-natural nucleic acid can also be used. The nucleotide analog is represented as a polyphosphate, usually with n from 2 (triphosphate) to 6 (heptaphosphate). At the end of the polyphosphate portion of the nucleotide analog is a group R. R can be either labeled or unlabeled. In some embodiments, R is —OH. R can be chosen, for example to have the polarity, charge, and H-bonding characteristics to improve its compatibility with the polymerase enzyme, and or to modulate its reactivity. The polymerase enzyme, the primer, or the template nucleic acid are generally bound to a substrate or otherwise held in place such that multiple sequential nucleotide analog additions can be observed.

Each of the types of nucleotide analogs will diffuse within the volume of the reaction and will sample the polymerase. Where one of the nucleotide analogs is complementary to the next available nucleotide within the template nucleic acid (i.e. the nucleotide analog is the cognate nucleotide analog), it will associate with the polymerase enzyme in position for incorporation. The nucleotide analog will then become incorporated into the growing strand, releasing the portion of the polyphosphate beyond the alpha phosphate. At this point, while the nucleotide analog has now been incorporated, the 3' hydroxyl of the growing nucleic acid is blocked by the labeled 3' hydroxyl leaving group and therefore will not extend further. At this point the selective cleaving activity, which cleaves the 3' hydroxyl leaving group more effectively after it is incorporated than when the nucleotide analog is unincorporated, cleaves the labeled leaving group, releasing the label into solution and freeing the 3' hydroxyl for addition to the next nucleotide analog. This set of steps repeats again with the addition of the next cognate nucleotide analog to the growing chain. The selective cleaving activity has been present throughout the process, such that the sequential incorporation of nucleotide analogs occurs without intervention by the user between the steps. No flushing in and out of reagents or flashing of light for photocleavage is required.

While the above sequential addition of nucleotide analogs is proceeding, the polymerase reaction is observed, for example by observing the fluorescence from the label. The polymerase reaction is observed under conditions in which the background from the unincorporated nucleotides and from the cleaved label is lowered such that the signal from labels associated with the polymerase enzyme can be distinguished. The lowering of the background can be accomplished, for example, by immobilizing the polymerase or template within an optical confinement such as a ZMW. For example, diffusion of a labeled nucleotide analog will be relatively fast, and the signal from labels which diffuse through an observation volume will produce a relatively short pulse. Signals from a nucleotide analog that associates with the polymerase, becomes incorporated, then has its 3' hydroxyl leaving group cleaved and released will be longer than the peaks from labels which diffuse through the observation volume, in some cases by orders of magnitude. Other signal attributes than peak width can be used to distinguish a label associated with the immobilized enzyme from freely diffusing label such as polarization, frequency, or peak shape.

For the methods of the invention, the label is held within the observation volume for the time it takes to complete two separate chemical steps. In this case, the first chemical step is the nucleotide analog incorporation step, which attaches the nucleotide to the growing chain, releasing the polyphosphate, and the second chemical step is the cleavage of the 3' hydroxyl leaving group. The time it takes both of the chemical steps to occur will generally be longer than for one step to occur. Where the two chemical steps have rates that are similar, the fraction of events that occur at fast times which are therefore difficult to detect can also be reduced as described in U.S. patent application Ser. No. 12/414,191 filed Mar. 30, 2009.

FIG. 1B shows an exemplary method of the invention in which an exonuclease activity comprises the selective cleaving activity. A plurality of nucleotide analogs which can act as substrates for an exonuclease after they have been incorporated into a growing strand are provided.

The nucleotide analogs have a label on a portion of the molecule that is cleaved by the exonuclease. In the example shown in FIG. 1B, the nucleotide analog has a phosphate linkage and a deoxyribose sugar moiety attached to the 3' hydroxyl group of the nucleotide portion of the nucleotide analog. The group attached to the 3' hydroxy position can be chosen such that the group is effectively removed by the exonuclease. In some cases, having a phosphate and sugar moiety in the arrangement shown provides a substrate which the exonuclease sees as a good substrate, allowing for facile removal by the exonuclease. The deoxyribose portion of the 3' hydroxyl leaving group has an —$OT_1$ at its 3 position. The substituent $T_1$ is chosen such that the polymerase enzyme will not extend the growing chain at this position, and that the nucleotide analog will be a substrate for the polymerase and exonuclease activities. $T_1$ can be, for example, H, methyl, ethyl, hydroxymethyl, or a small alkyl or aryl group generally having fewer than 6 carbons. The nucleotide analogs need not have the particular structure shown in order to carry out the methods of the invention. The nucleotide analogs of the invention will generally comprise a labeled leaving group at its 3' hydroxyl that will act as a substrate for an exonuclease activity to cleave the labeled leaving group.

The sequencing reaction mixture also comprises a polymerase enzyme, a template nucleic acid, a primer, a selective cleaving agent, and the components necessary for carrying out nucleic acid additions to a growing nucleic acid strand complementary to the template. For this example, four nucleotide analogs, each having a nucleobase B corresponding to A, G, T, and C, are included in the mixture. Each of the four nucleotide analogs has a different, independently observable label, for example a fluorescent dye label. In this exemplary embodiment, the label is attached to the 1 position on the deoxyribose of the 3' hydroxyl leaving group. In some cases the label comprises or is attached to a purine or pyrimidine moiety chosen to act as an effective substrate for the exonuclease enzyme. The label may be attached with by a liker. In some cases the linker can be a short, rigid linker such as an allyl or propargyl linker, or can be a longer more flexible linker, such as any suitable linker described herein. The label need not be at this position, but can be on any suitable position on the leaving group portion of the nucleotide analog. The polymerase enzyme, the primer, or the template nucleic acid are generally bound to a substrate or otherwise held in place such that multiple sequential nucleotide analog additions can be observed.

Here, the nucleotide analog has phosphate group attached to the 3' hydroxyl group. In some cases, a phosphate in this portion of the 3' hydroxyl leaving group is useful in having the 3' hydroxyl leaving group act as an effective substrate for the exonuclease activity. The nucleotide analog shown has is a polyphosphate at the 5' position, usually having n with a value from 2 (triphosphate) to 6 (heptaphosphate). At the end of the polyphosphate portion of the nucleotide analog is a group R. R can be either labeled or unlabeled. In some embodiments, R is —OH. R can be chosen, for example to have the polarity, charge, and H-bonding characteristics to improve its compatibility with the polymerase enzyme, and or to modulate its reactivity.

As with the system described in FIG. 1A, each of the types of nucleotide analogs will diffuse within the volume of the reaction and will sample the polymerase. Where one of the nucleotide analogs is complementary to the next available nucleotide within the template nucleic acid (i.e. the nucleotide analog is the cognate nucleotide analog), it will associate with the polymerase enzyme in position for incorporation. The nucleotide analog will then become incorporated into the growing strand, releasing the portion of the polyphosphate beyond the alpha phosphate. At this point, the nucleotide analog has been incorporated, and because the 3' hydroxyl of the growing nucleic acid is blocked, no further extension of the growing strand will occur until the 3' hydroxyl leaving group is removed.

The exonuclease activity then cleaves the portion of the nucleotide analog beyond the 3' hydroxyl of the first nucleotide portion of the dinucleotide. The exonuclease activity is selected such that it has higher activity for an incorporated than for an unincorporated nucleotide analog such as a dinucleotide polyphosphate. Template dependent 3'-5' exonuclease activity generally act on double stranded nucleic acids, but to have little or substantially no activity for single stranded nucleic acids including dinucleotides such as the nucleotide analogs shown in FIG. 1B. The exonuclease activity cleaves the portion of the nucleotide analog having the labeled leaving group, releasing the label into solution and freeing the 3' hydroxyl on the first nucleotide portion of the dinucleotide for addition to the next nucleotide analog. This set of steps repeats again with the addition of the next cognate nucleotide analog to the growing chain. The exonuclease selective cleaving activity is present throughout the process, such that the sequential incorporation of nucleotide analogs occurs without intervention by the user between the steps. No flushing in and out of reagents or flashing of light for photocleavage is required. The observation of the sequential incorporation of the nucleotides having the different labels provides sequence information about the template nucleic acid.

Figure 2:
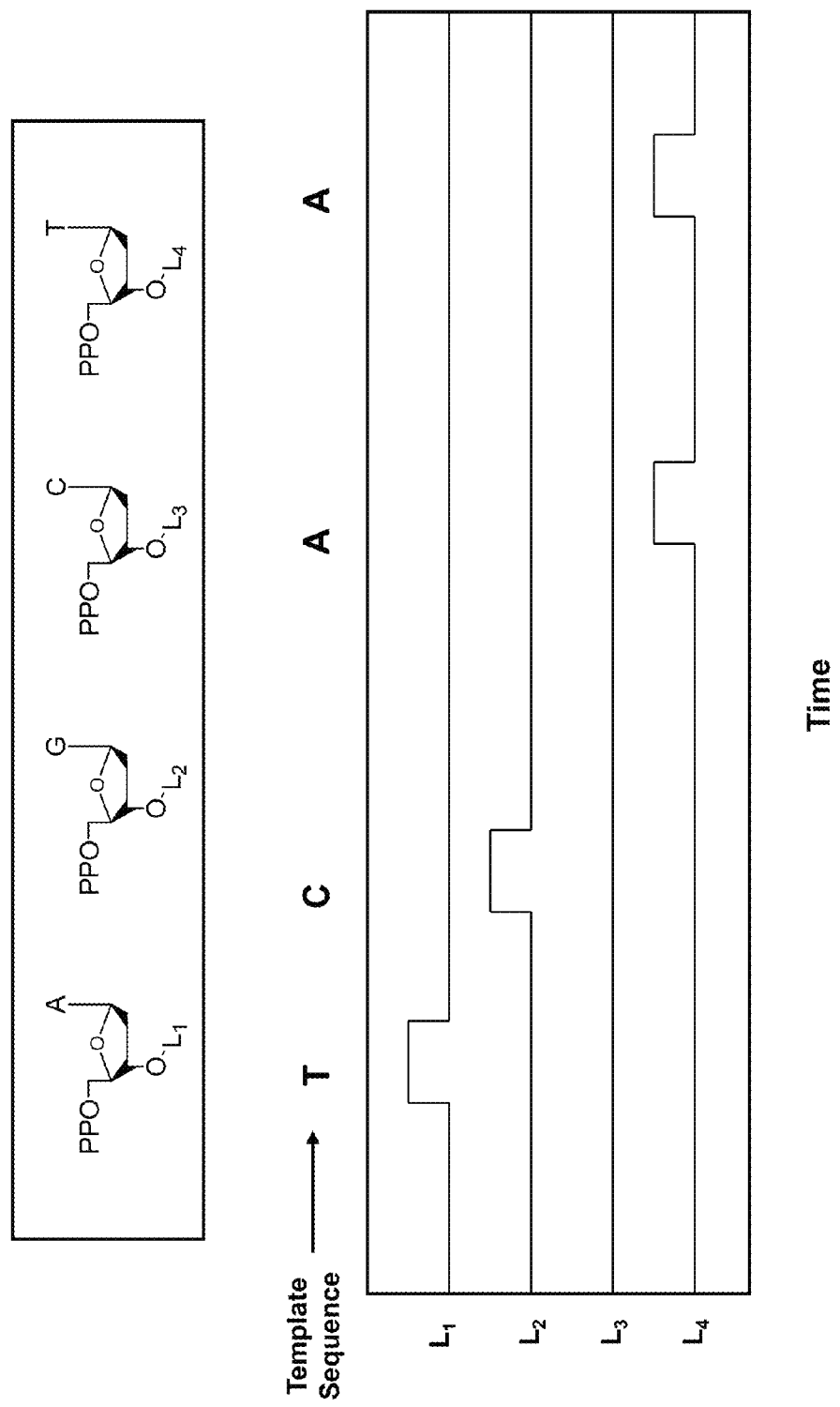
FIG. 2 shows how measuring intensity versus time for four nucleotide analogs comprising 3' hydroxy leaving group labels can be used to determine the sequence of a template nucleic acid.

FIG. 2 shows how some of the methods of the invention can be used to determine a portion of the sequence of a template nucleic acid. For this example, a sequencing reaction mixture has four types of nucleotide analogs, each having a different label. Here, the nucleotide analog corresponding to A has a labeled 3' hydroxyl leaving group labeled with $L_1$, the nucleotide analog corresponding to G has a labeled 3' hydroxyl leaving group labeled with $L_2$, the nucleotide analog corresponding to C has a labeled 3' hydroxyl leaving group labeled with $L_3$, and the nucleotide analog corresponding to T has a labeled 3' hydroxyl leaving group labeled with $L_4$. The labels, are for example, fluorescent dyes which are spectrally separated such that they can be simultaneously monitored. The sequencing mixture includes a polymerase enzyme, a primed nucleic acid template, a selective cleaving activity such as an exonuclease activity and the other components required for carrying out polymerase mediated nucleic acid synthesis. Either the polymerase or template is immobilized on a substrate in a manner in which sequential nucleotide additions to one strand can be monitored. The labels are excited with either one or two excitation sources, and the fluorescent emissions from each of the dyes is observed using one or more detectors. All four channels are concurrently monitored.

The plot in FIG. 2 represents fluorescence intensity for each of the four dyes as a function of time. A first peak is observed in the channel corresponding to $L_1$. The peak results from to the association of the nucleotide analog corresponding to A associating with the polymerase enzyme, the incorporation of the nucleotide analog, the release of polyphosphate, and the cleavage and release of the 3' hydroxyl leaving group comprising label $L_1$. Once the 3' hydroxyl leaving group is cleaved, for example by the exonuclease activity, it is released into solution, and the intensity of the $L_1$ signal drops back down to the baseline. The incorporation of an A nucleotide analog indicates that the template nucleic acid has a T at the corresponding position. The next peak that is observed is in the channel corresponding to $L_2$. This peak indicates an association and subsequent incorporation of the nucleotide analog corresponding to G, indicating that there is a C at the next position in the template nucleic acid. Third and fourth peaks are observed in the channel corresponding to $L_4$, indicating the incorporation of a nucleotide analog having a T, thus indicating that the next two nucleotide residues in the template nucleic acid are A and A. In this manner, by directly observing both polymerase incorporation, and exonuclease cleavage at the single molecule level, the sequence of a portion of a template nucleic acid can be determined. This process can be multiplexed by concurrently observing multiple polymerase reactions, for example at different positions on a substrate. While observing these reactions, there can be other peaks which are observed that are not indicative of an incorporation event. For example, labeled nucleotide analogs diffusing in and out of the observation region can give rise to peaks. Also, peaks may be observed due to cognate or non-cognate nucleotide analogs associating with the polymerase enzyme, but not incorporating (branching or non-cognate extra). These types of peaks can be differentiated from true incorporation events by their peak characteristics, for example by peak width, peak shape, or polarization characteristics.

In some aspects of the invention, nucleotide analogs having two separately cleavable labeled leaving groups are used. By having two separately cleavable leaving groups, signals corresponding to incorporation will have even more distinct characteristics from non-incorporation peaks than systems that do not have two separately cleavable leaving groups.

Figure 3:
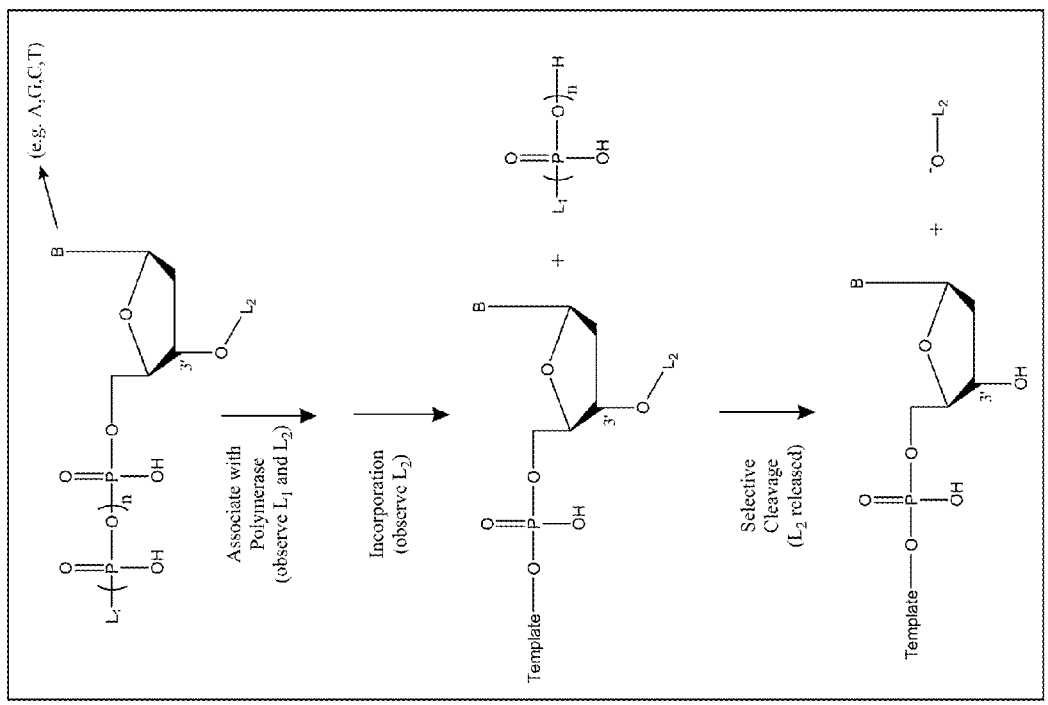
FIG. 3 shows an embodiment of a single molecule sequencing method of the invention which is performed using nucleotide analogs, each having both a polyphosphate label and a 3' hydroxyl leaving group label.

FIG. 3 shows one embodiment of the invention that incorporates two separately cleavable labels. A plurality of nucleotide analogs are provided in a sequencing reaction mixture. Here, four types of nucleotides are provided, corresponding to A, G, C, and T. Each of the nucleotides has at least one label that is different from the label on the other three nucleotide analogs. Each of the nucleotide analogs has one label attached to the polyphosphate portion of the nucleotide analog (L1) and a second label (L2) attached to the 3' leaving group. For the purposes of this example the labels L1 and L2 are substantially non-interacting labels. In other cases, as described herein, the labels can interact, for example by FRET or quenching. The sequencing reaction mixture also comprises a polymerase enzyme, a template nucleic acid, a primer, a selective cleaving agent, and the components necessary for carrying out nucleic acid additions to a growing nucleic acid strand complementary to the template. Either the polymerase or the nucleic acid template is generally immobilized for viewing over sequential nucleotide analog additions.

The plurality of nucleotide analogs samples the polymerase enzyme. A nucleotide analog that is complementary to the next nucleotide on the template (the cognate nucleotide analog) associates with the polymerase and becomes incorporated into the growing strand, releasing the pyrophosphate portion beyond the alpha phosphate, thus releasing the label L1. During the time period from association to release of the label L1, signals from both label L1 and label L2 are observed. Upon the release of label L1, a signal from L1 is no longer observed, but the signal from L2 continues to be observed until selective cleavage of the 3' hydroxyl group occurs, releasing the 3' hydroxyl leaving group along with label L2. Thus, this process produces a set of characteristic signals for nucleotide analog incorporation in which both L1 and L2 are observed for a time period, then L2 extends for another time period. Having a characteristic set of signals provides more information for distinguishing a true incorporation event from other signals. For example, in this system, the sampling of the enzyme by cognate or non-cognate nucleotide analogs will generally provide a peak showing both L1 and L2, with no L2 peak extending beyond the release of L1. Where the labels L1 and L2 interact, other signals characteristic of incorporation events can be generated as described herein. Generally each of the A, G, C, T nucleotide analogs will have either a unique label L1, a unique label L2 or both a unique L1 and L2, allowing for distinguishing which nucleotide has been incorporated.

Figure 4:
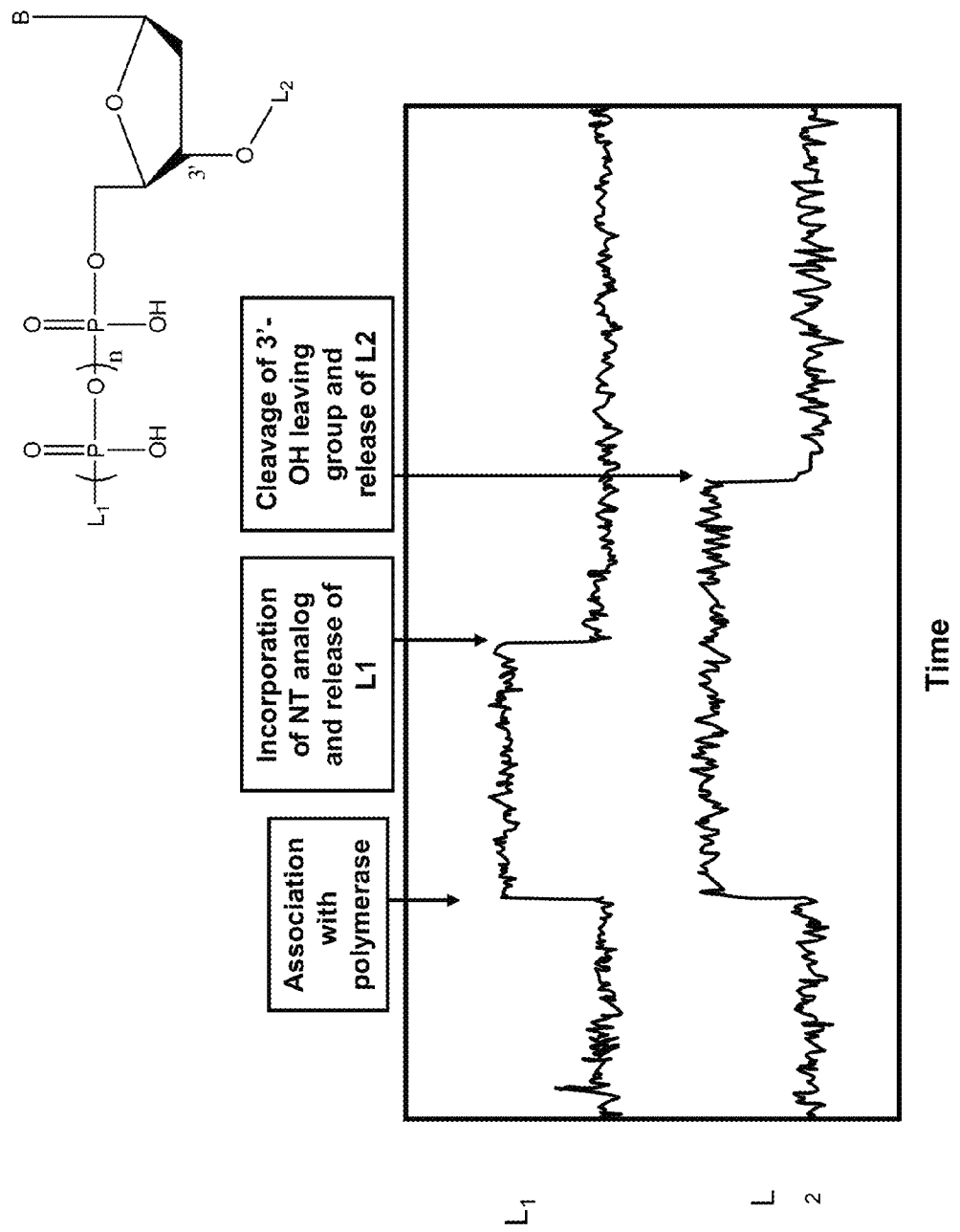
FIG. 4 illustrates how two non-interacting labels, one on the polyphosphate and one on the 3' hydroxyl can produce an intensity versus time signal that is indicative of incorporation.

FIG. 4 shows an example of the type of signal which could be observed using non-interacting, separately cleavable labels. The signal from labels L1 and L2 are concurrently observed during the polymerase reaction at a single molecule level. When the nucleotide analog associates with the enzyme, the intensity of both $L_1$ and $L_2$ rises. The intensity of both $L_1$ and $L_2$ remains high until the nucleotide analog is incorporated into the growing nucleic acid strand and the polyphosphate beyond the alpha phosphate comprising $L_1$ is released into solution, at which point the signal from $L_1$ drops to baseline, resulting in a peak in the $L_1$ channel. The signal from $L_2$ remains high until the selective cleaving activity such as the exonuclease activity cleaves the 3' hydroxyl leaving group comprising label $L_2$, releasing $L_2$ into solution. The observation of peaks for $L_1$ and $L_2$ which begin at the same time, and for which the peak corresponding to $L_1$ is shorter than the peak corresponding to $L_2$, and having durations consistent with the cleavage steps provides the strong likelihood that an incorporation event for that nucleotide analog has occurred.

Figure 5:
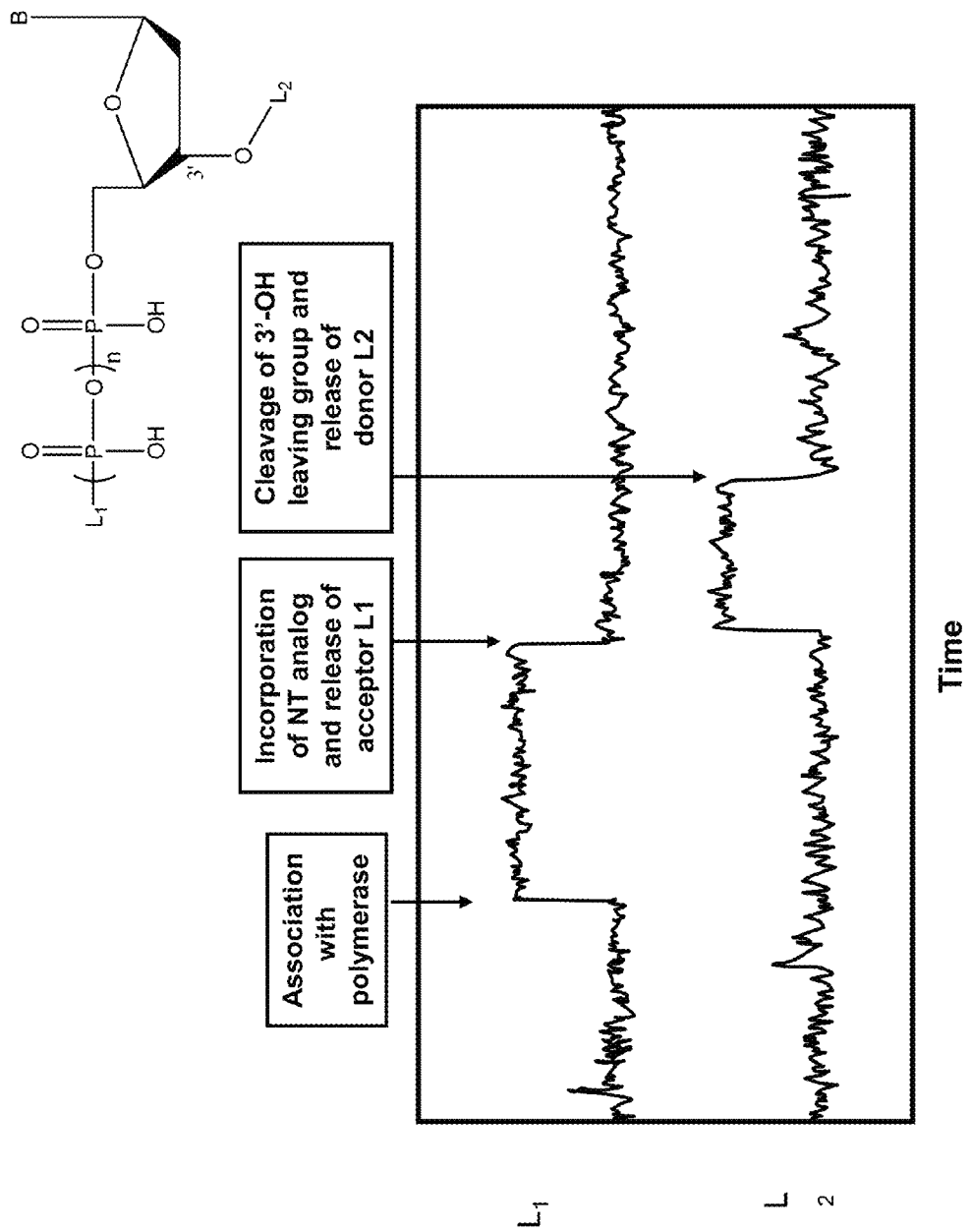
FIG. 5 illustrates how two interacting labels, one FRET acceptor on the polyphosphate and one FRET donor on the 3' hydroxyl can produce an intensity versus time signal that is indicative of incorporation.

FIG. 5 shows an example of the type of signal which could be observed using a nucleotide analog having labels $L_1$ and $L_2$ which interact, for example by FRET. In the example shown, $L_1$ is a FRET acceptor and $L_2$ is a FRET donor. Here, $L_1$ and $L_2$ are chosen, and the linker molecules are designed such that when $L_1$ and $L_2$ are attached to the nucleotide analog, substantially all of the fluorescence from the donor-acceptor will be from the acceptor $L_2$. An optical system is used in which excitation light is provided such that it is absorbed by the donor $L_2$. When the nucleotide analog associates with the enzyme, the signal from acceptor $L_1$ rises, and remains high while the nucleotide analog is associated with the polymerase enzyme. When the nucleotide is incorporated into the growing strand, the polyphosphate portion of the nucleotide beyond the alpha phosphate is cleaved and released along with acceptor $L_1$. When $L_1$ is cleaved, there is no more FRET interaction with the donor $L_2$, and since it is no longer transferring its energy to the acceptor $L_1$, fluorescence from the donor $L_2$ is observed. The fluorescent signal from $L_2$ persists until the 3' hydroxyl leaving group bearing $L_2$ is cleaved. Thus, this system provides a characteristic set of signals that are highly indicative of nucleotide incorporation. Here, the observation of a signal from L1 followed immediately by a signal from L2, each having the pulse characteristics consistent with the respective cleavage steps provides a high level of confidence that an incorporation event for that nucleotide analog has occurred. For example, this type of signal would not be observed where cognate or non-cognate nucleotide analogs are sampling the active site of the polymerase, as in such cases, no release of L1 would occur and therefore no donor L2 peak would be observed. For this example, excitation light which is absorbed by L2 but not by L1 is used. In some cases, illumination and detection schemes can be used in which fluorescence contributions from both the donor and acceptor can be observed.

Figure 6:
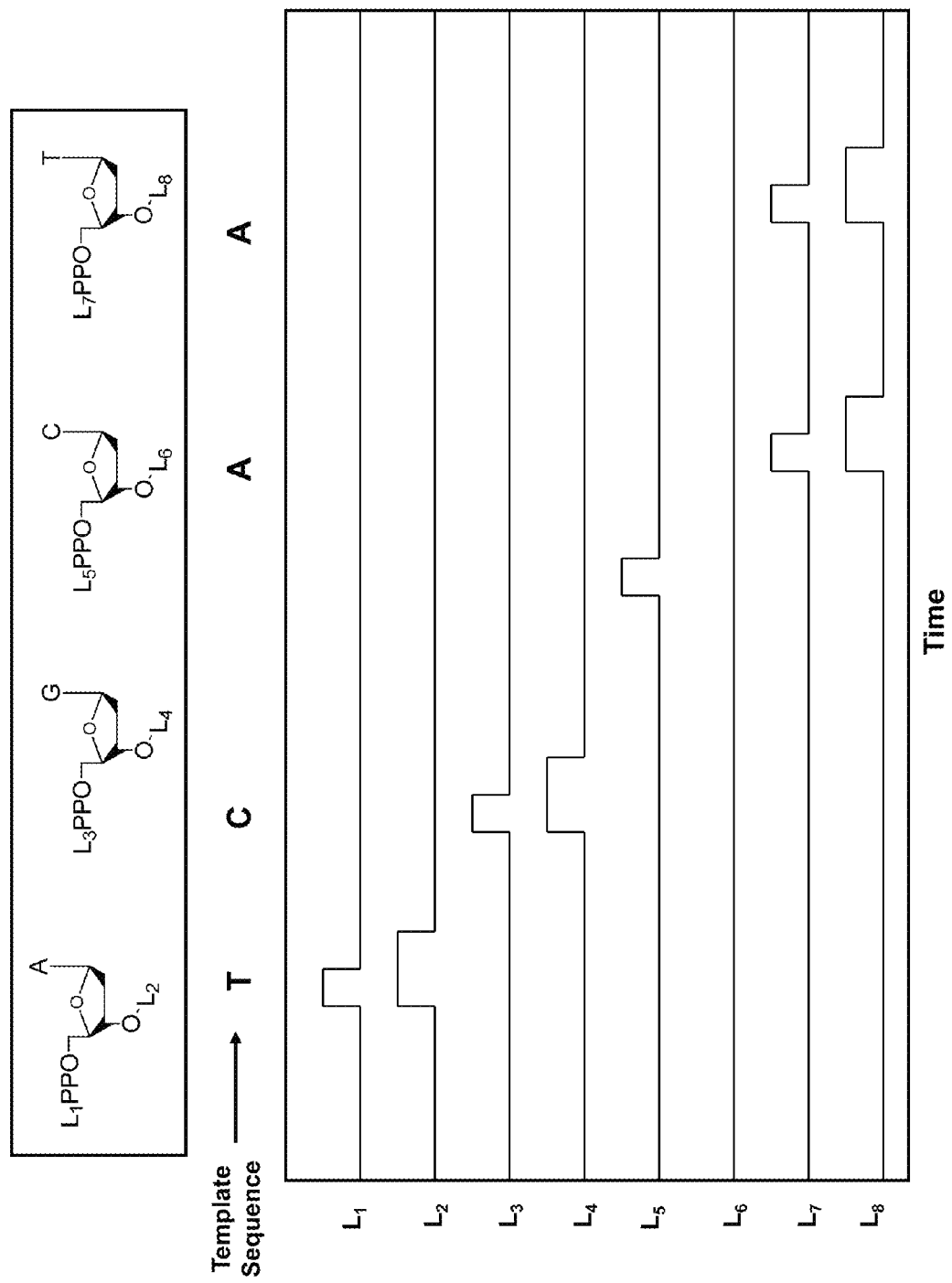
FIG. 6 illustrates a sequencing run using four nucleotide analogs, each nucleotide analog having a unique polyphosphate label and a unique 3' hydroxyl labels.

FIG. 6 shows how a system having four types of nucleotide analogs, each with a unique label on its polyphosphate and a unique label on its 3' hydroxyl leaving group, can be used to determine a portion of the sequence of a template nucleic acid. Here, the nucleotide analog corresponding to A has a polyphosphate labeled with L1 and a 3' hydroxyl leaving group labeled with L2, the nucleotide analog corresponding to G has a polyphosphate labeled with L3 and a 3' hydroxyl leaving group labeled with L4, the nucleotide analog corresponding to C has a polyphosphate labeled with L5 and a 3' hydroxyl leaving group labeled with L6, and the nucleotide analog corresponding to T has a polyphosphate labeled with L7 and a 3' hydroxyl leaving group labeled with L8. The labels are, for example, fluorescent dyes which are spectrally separated such that they can be simultaneously monitored. The sequencing mixture includes a polymerase enzyme, a primed nucleic acid template, a selective cleaving activity such as an exonuclease activity and the other components required for carrying out polymerase mediated nucleic acid synthesis. Either the polymerase or template is immobilized on a substrate in a manner in which sequential nucleotide additions to one strand can be monitored. The labels are excited with either one or two excitation sources, and the fluorescent emissions from each of the dyes is observed using one or more detectors. All eight channels are concurrently monitored. For the example described, the dyes on the polyphosphate and 3' hydroxyl are non-interacting.

In the fluorescent intensity versus time plot of FIG. 6 a polymerase reaction is monitored. First, signals are observed in L1 and L2 having the characteristics of incorporation described above in which the signal from the label on the polyphosphate L1 and signal from the label on the 3' hydroxyl L2 rise simultaneously, and the signal from L1 has a shorter pulse width than that for L2. This set of signals is consistent with L1 being cleaved and released upon incorporation and L2 being subsequently cleaved and released by the selective cleaving activity such as an exonuclease activity. Thus, the characteristic set of peaks from L1 and L2 indicate the incorporation of A, indicating that the template nucleic acid has a T at this position. Characteristic incorporation signals are then observed in the L3 and L4 channels indicating the incorporation of G, indicating that the template nucleic acid has a C in this position. A signal is then observed in the L5 channel, but the signal does not have the characteristics of incorporation, and is not used to call a base on the template nucleic acid. Two sets of characteristic incorporation peaks are then observed in channels L7 and L8 indicating the incorporation of two nucleotide analogs corresponding to T, and this indicating that the template nucleic acid has an A and an A in the next two positions. In this manner, the sequence of the template nucleic acid can be determined.

Figure 7:
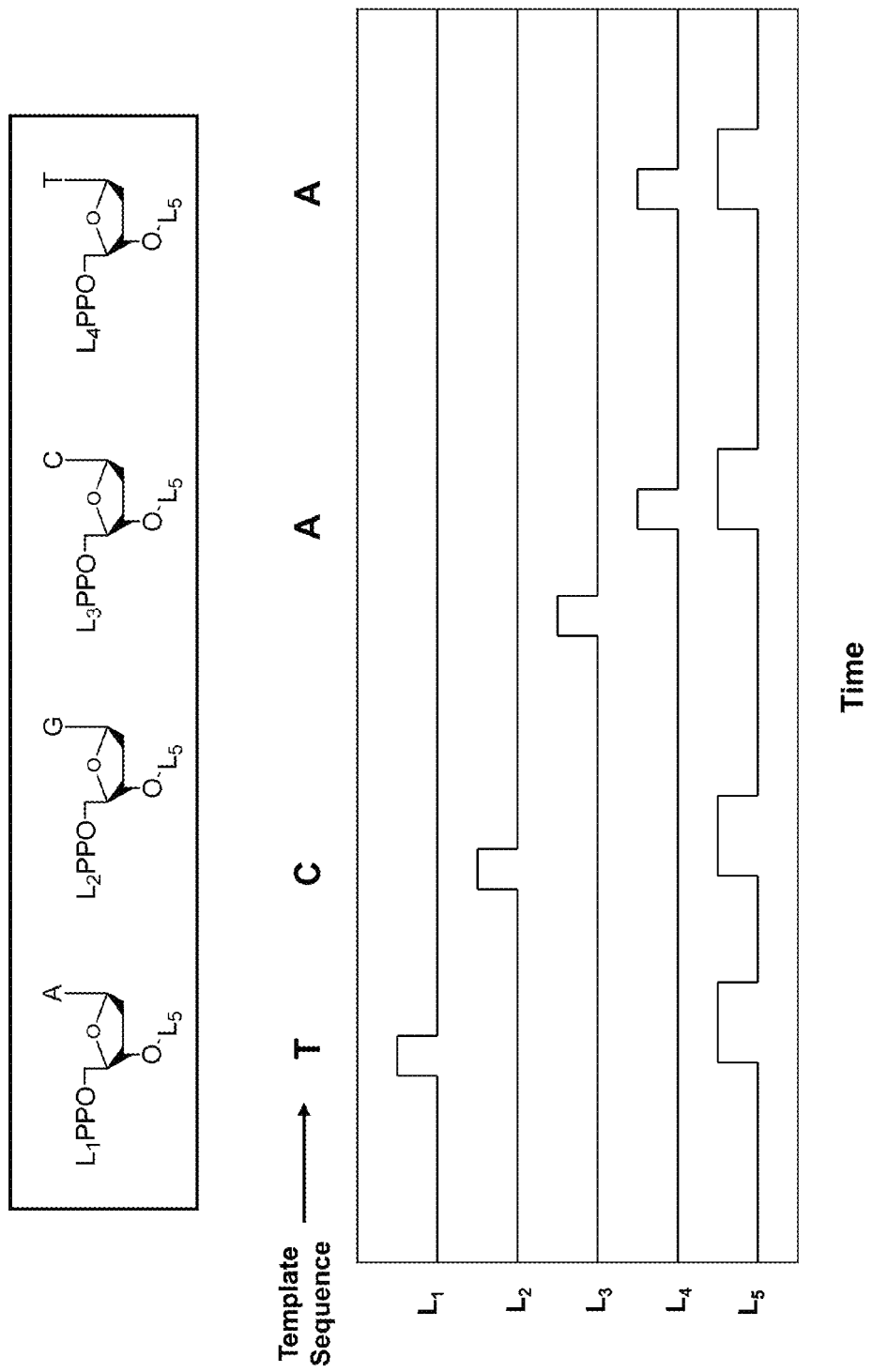
FIG. 7 illustrates a sequencing run using four nucleotide analogs, each nucleotide analog having a unique polyphosphate label and each having the same 3' hydroxyl label.

FIG. 7 shows a sequencing method of the invention in which each of the nucleotide analogs has a unique polyphosphate label, and each has the same 3' hydroxyl leaving group label. Here, the nucleotide analog corresponding to A has the polyphosphate label $L_1$, the nucleotide analog corresponding to G has the polyphosphate label $L_2$, the nucleotide analog corresponding to C has the polyphosphate label $L_3$, the nucleotide analog corresponding to T has the polyphosphate label $L_4$. Each of the four nucleotide analogs is labeled on its 3' hydroxyl leaving group with the label $L_5$. In the sequencing reaction of FIG. 7, a peak is observed in the $L_1$ channel. A peak beginning at the same time as the $L_1$ peak and extending beyond time of the $L_1$ peak is observed in the $L_5$ channel. These peaks have the characteristics consistent with an incorporation event un which the polyphosphate label $L_1$ is cleaved and released upon incorporation of the nucleotide analog into the growing chain, and then the 3' hydroxyl label $L_5$ is cleaved by the selective cleaving activity, for example exonuclease activity. The incorporation event associated with $L_1$ indicates that an A nucleotide analog has been incorporated, indicating that the template nucleic acid has a T in that position. A signal is then observed in the $L_2$ channel, also having the corresponding characteristic peak in $L_5$, indicating that a G has been incorporated, and thus that the template has a C in this position. Next a signal is observed in the $L_3$ channel. However, for this peak, no corresponding peak is observed in the $L_5$ channel, indicating that this peak does not correspond to an incorporation. Following this event, two peaks are observed in the $L_4$ channel, and for each, a corresponding characteristic peak in $L_5$ is observed, indicating that two T nucleotide analogs have been incorporated, and that the next two nucleotides in the template nucleic acid sequence are A and A.

Where a set of nucleotide analogs each having two labeled cleaving groups are used, there are a number of different combinations of dyes that can be employed. In general, each type of nucleotide analog will have at least one label that is unique to that nucleotide analog. In some cases, the labels on the polyphosphate will comprise the set of unique labels. In some cases, the labels on the 3' hydroxyl leaving group comprise the set of unique labels. In some cases there is a combination of unique labels for the set of nucleotides, with some being on the polyphosphate and some being on the 3' hydroxyl leaving groups. In some cases each of the nucleotide analogs has both a unique polyphosphate label and a unique 3' hydroxyl leaving group label. The decision of which and how many unique labels to employ will depend on the particular system that is used. For example, a system having four unique polyphosphate fluorescent labels and four unique 3' hydroxyl fluorescent labels would provide a distinct set of signals for each nucleotide analog, each of which would be represented by signals in two independent channels, improving the ability to make the correct base call; but this system would require eight independently resolvable dyes, each of which requiring effective excitation. The ability to choose the number of unique dyes that are used allows for optimizing the performance and complexity of the system. The number and types of unique dyes that are used is also influenced by whether the system utilizes dye interactions such as FRET or quenching as described herein in more detail.

In many cases, sequencing systems will utilize four unique nucleotide analogs, for example corresponding to A, C, G, and T or A, C, G, and U. These four nucleotide analog systems can employ, for example, four unique polyphosphate labels and four unique 3' hydroxyl labels, utilizing eight different labels; four unique polyphosphate labels and one 3' hydroxyl label, utilizing five different labels; four unique polyphosphate labels and two unique 3' hydroxyl labels, utilizing six different labels; one polyphosphate label and four unique 3' hydroxyl labels, utilizing five different labels; or two polyphosphate label and four unique 3' hydroxyl labels, utilizing six different labels.

The choice of which labels and how many labels are used is influenced by whether or not the labels are interacting. For example, for FRET systems, in some cases the donor is on a polyphosphate (PP) label and the acceptor is on a 3' hydroxyl leaving group label. In these cases, generally the acceptor fluorescence will be observed from the time at which NT analog associates with the polymerase until the PP is cleaved after incorporation and the donor is cleaved; at which point, only the acceptor is attached to the nucleotide analog. Depending on how the excitation is delivered, fluorescence from the acceptor may or may not be observed after cleavage of the donor. For example, if excitation light is provided which only excites the donor and provides no excitation to the acceptor, then after the donor is cleaved no further acceptor fluorescence will be observed. If, however, excitation light is provided which excites both the donor and acceptor, then acceptor fluorescence may be observed after cleavage of the donor until cleavage of the 3' hydroxyl and release of the acceptor. Excitation light can be provided which excites the donor more effectively than the acceptor, resulting in a drop in the level of fluorescence upon cleavage of the PP and the donor. This could result in a two step fluorescence signal in a single fluorescence channel indicative of incorporation.

In some cases, the acceptor is on the polyphosphate label and the donor is on a 3' hydroxyl leaving group label. In these cases, generally fluorescence from the acceptor will be observed from association of the nucleotide analog with the enzyme until cleavage of PP and release of the acceptor. At this point fluorescence from the donor can be observed until the 3' hydroxyl leaving group comprising the donor is cleaved and released. This approach provides a characteristic signal of incorporation in which there is a pulse in the acceptor channel followed directly by a pulse in the donor channel. This approach has the advantage that there are signals in two separate channels that are combined to identify an incorporation event.

As described above, for a given system, it is usually desirable to have at least one unique dye per nucleotide analog in order to identify the nucleotide analog upon incorporation. In the FRET system having four nucleotide analogs, there can be, in some embodiments, eight distinct labels, four on the polyphosphate and four on the 3' hydroxyl leaving group. In some embodiments, four nucleotide analogs are used, each having a unique acceptor on its polyphosphate, and all four nucleotide analogs having the same donor on the 3' hydroxyl leaving group. In some cases, it may be desirable to have more than one donor for all four of the acceptor labels. For example, in some cases, four nucleotide analogs are used, each having a unique acceptor, two having one donor, and the other two having a second donor. For these cases, it may be desirable to provide two excitation sources, one to excite one donor, and the other to excite the other donor.

In some cases the labels on the polyphosphate and the 3' hydroxyl leaving group will interact by quenching. The systems which interact by quenching will generally have a dye and a quencher. In some cases, the quencher will also have a fluorescent signal which is observable when it is not quenching the dye. The systems which utilize quenchers can be desirable, because, since the signal from the nucleotide analogs is quenched until PP cleavage occurs, the background signal from the nucleotide analogs is lower than for non-quenched systems. In some embodiments the quencher is on the 3' hydroxyl leaving group and the dye that is quenched is on polyphosphate. In these cases, no signal will be seen from association until cleavage of the PP on incorporation of the nucleotide analog into the growing chain. After cleavage of the PP and release of the dye, the signal from the quencher may be observed. In some embodiments, the quencher is on the PP and the dye is on the 3' hydroxyl leaving group. For these cases, generally, no signal will be observed from association until cleavage of the PP upon incorporation of the nucleotide analog and release of the quencher. From this point until cleavage of the 3' hydroxyl leaving group, signal from the unquenched dye on the 3' hydroxyl can be observed.

In some cases, the 3' hydroxyl can be blocked from further polymerization without the 3' hydroxyl itself having a covalently bound leaving group. For example, "virtual reversible terminators", which have substituents attached to the base portion of the nucleotide analog that can be used which block further nucleotide analog incorporations by having cleavable groups attached to the bases of the nucleotide analogs which block extension of the growing strand. Bowers et al., Nature Methods, 6(8), 593, 2009. In some embodiments of the invention the nucleotide analogs have substituents that block further nucleic acid synthesis and that are substrates for the selective cleaving activity such as an exonuclease activity wherein the selective cleaving activity removes the virtual reversible terminator during the polymerase reaction in the same manner described above for direct covalent blocking of the 3' hydroxyl.

The methods of the invention can be carried out using any suitable 3'-unblocked reversible terminators. LaserGen, Inc. has showed that a small terminating group attached to the base of a 3'-unblocked nucleotide can act as an effective reversible terminator and be efficiently incorporated by wild-type DNA polymerases. Suitable 3' unblocked reversible terminators include Lightning Terminators. Appropriate reversible terminators include virtual terminators that are 3'-unblocked terminators with a second nucleoside analogue that acts as an inhibitor. The 3'-unblocked terminators should have, for example modifications to the terminating or inhibiting groups so that DNA synthesis is terminated after a single base addition. In some cases, cleavage of only a single bond is required to remove both the terminating or inhibiting group and the fluorophore group from the nucleobase, providing an efficient strategy for restoring the nucleotide for the next CRT cycle Selective Cleaving Activity The selective cleaving activity is an activity that selectively cleaves the leaving group from the 3' hydroxyl of the nucleotide analog after it has been incorporated into the growing nucleotide strand. After incorporation, the nucleotide analog is generally part of a double-stranded nucleic acid. In the methods of the invention, the selective cleaving activity is present through multiple nucleotide incorporations and need not be repeatedly added for each nucleotide addition. The selective cleaving activity is generally highly selective for cleaving the 3' hydroxyl leaving group after the nucleotide analog has been incorporated and not cleaving the 3' hydroxyl leaving group in unincorporated nucleotide analogs. In some embodiments selective cleaving group will cleave an incorporated 3' hydroxyl leaving group at least 10 times more effectively than cleaving an unincorporated 3' hydroxyl leaving group. In some embodiments selective cleaving group will cleave an incorporated 3' hydroxyl leaving group at least 100 times more effectively than cleaving an unincorporated 3' hydroxyl leaving group. In some embodiments selective cleaving group will cleave an incorporated 3' hydroxyl leaving group at least 1000 times more effectively than cleaving an unincorporated 3' hydroxyl leaving group. In some embodiments selective cleaving group will cleave an incorporated 3' hydroxyl leaving group at least 10,000 times more effectively than cleaving an unincorporated 3' hydroxyl leaving group.

The selective cleaving activity can exploit one or more differences between an incorporated and unincorporated 3' hydroxyl leaving group. One significant difference is that the incorporated nucleotide is generally part of a double stranded nucleic acid. This difference can be exploited, for example, by enzymes that selectively react with double stranded nucleic acids such as dsDNA or dsRNA. Another difference is that at the point right after the nucleotide analog is incorporated, the nucleotide analog is held within or near the active site of the polymerase enzyme. The environment within the enzyme can be significantly different than in the surrounding solution, for example in its polarity, H-bonding, and/or ionic strength. In addition, the proximity of reactive or interactive functional groups such as —OH, —SH, —NH2, imidazole, can be used to increase the relative rate of a cleavage reaction. In some embodiments, the selective cleaving activity is an exonuclease activity that is part of the polymerase enzyme itself. An exonuclease activity that is part of the polymerase activity can exploit both the proximity of the newly incorporated nucleotide analog, and the preference for a double stranded substrate. In some cases, an enzyme activity other than exonuclease activity can be held near the polymerase active site, for example by creating a fusion protein with the polymerase and the portion of the enzyme providing the selective cleaving activity.

Another difference for the incorporated versus unincorporated 3' hydroxyl leaving group is that the incorporated 3' hydroxyl leaving group is generally attached to a molecule that is immobilized on a substrate, either through the double stranded nucleic acid if the template or primer is bound to the substrate, or through the polymerase enzyme if the polymerase is bound to the surface. Thus, by localizing a selective cleaving activity on the substrate in proximity to the polymerase enzyme or double stranded DNA, the activity can be made to be significantly more reactive to the nearby immobilized 3' hydroxyl leaving group than to a 3' hydroxyl leaving group free in solution.

Figure 8:
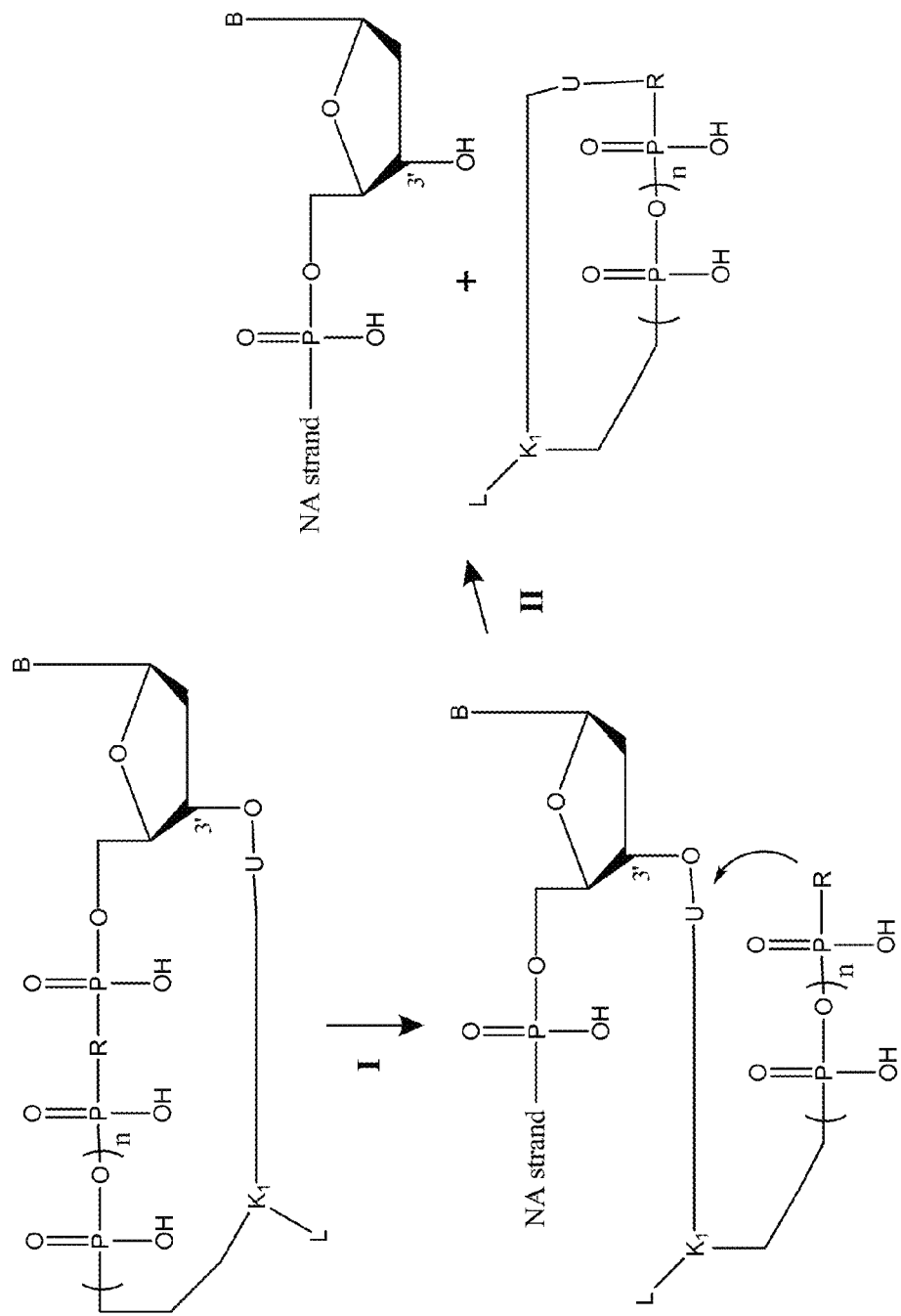
FIG. 8 shows an embodiment in which a cyclic nucleotide analog comprising a label is cleaved off in two separate chemical steps; first by a polymerase enzyme near the 5' hydroxyl, and second by intramolecular cleavage near the 3' hydroxyl of the nucleotide analog.

In some aspects, the methods of the invention can be carried out using a cyclic nucleotide analog having a cyclic portion formed by a connection between the 3' hydroxyl group and the 5' hydroxyl group of the nucleotide analog. FIG. 8 shows an embodiment of a method of the invention utilizing such a cyclic nucleotide analog. The cyclic nucleotide analog has a polyphosphate portion attached to the 5' hydroxyl of the nucleotide analog. As shown, the polyphosphate portion may have two, three, or more phosphates. The polyphosphate portion is connected to the 3' hydroxyl of the nucleotide analog through a linker K1 and a cleavable group U. The linker K1 can be any suitable linker molecule including the linkers described in more detail below. The cyclic nucleotide analog acts as a substrate for the polymerase enzyme, which cleaves the nucleotide analog in step I between the alpha and beta phosphates, attaching the growing nucleic acid strand to the alpha phosphate, and releasing the beta phosphate.

After step I and before step II, the nucleotide analog is not capable of a further nucleotide addition as its 3' hydroxyl group remains blocked. The cleaved beta phosphate is then capable of reacting with the cleavable moiety U through reactive group R in step II. This second cleavage reaction results in the release of a labeled cyclic leaving group, unblocking the 3' hydroxyl group and leaving it free for carrying out the addition of the next nucleotide analog. By using, for example, four cyclic nucleotide analogs, each with a nucleobase corresponding to A, G, T, or C, and each having a different, independently detectable label, the signal from the labels can be used to indicate which of the nucleotide analogs is associated with the enzyme, and therefore which nucleotide analog has been incorporated, thus allowing the sequencing of a template nucleic acid.

The reactive group R is selected such that it will react intramolecularly with the cleavable moiety U. For example, R can comprise a nucleophile such as a thiol group (—SH) which can nucleophilically attack an ester group U to release the 3' hydroxyl and cleave off the cyclic labeled leaving group. U can comprise, for example, a carboxylic ester, a phosphate ester, or a sulfonate ester. Where R comprises a nucleophile, it can be, for example, a nitrogen, oxygen, carbon, or sulfur nucleotide. In some cases, a catalyst is present in solution to catalyze the cleavage reaction. These cyclic nucleotide analogs provide for a selective cleavage of a 3' hydroxyl leaving group, such that the cleavage occurs after the nucleotide has been incorporated, and whereby little or substantially no cleavage of the 3' hydroxyl leaving group occurs before the nucleotide has been incorporated.

The selective cleaving activity can be an enzyme activity. There are a number of enzymes that perform a cleaving function which could be used to selectively cleave the 3' hydroxyl leaving group to expose the 3' hydroxyl group for further incorporations. Such enzymes include hydrolases, including esterases, nucleases, phosphodiesterases, phosphatases, peptidases, proteases, acid anhydride hydrolases, helicases, glycosylases, and glycoside hydrolases. Preferred enzyme selective activities comprise exonucleases. In order for an enzyme to act as the selective cleaving activity, the incorporated nucleic acid including the 3' hydroxyl leaving group must be a substrate for the enzyme. The linking group that connects the 3' hydroxyl to the label can be selected such that it will act as a substrate for the enzyme.

In some embodiments, pyrophosphorolysis can be used to remove the 3' hydroxyl leaving group. For such systems, the 3' hydroxyl leaving group would have two or more phosphates attached to the oxygen of the 3' hydroxyl of the nucleotide analog. A pyrophosphate activity, for example cleaves the two or more phosphates to release the 3' hydroxyl.

In some embodiments, a retroviral reverse transcriptase can be used to remove the 3' hydroxyl leaving group. Human immunodeficiency virus type 1 (HIV-1) reverse transcriptase (RT) and other retroviral RTs lack exonuclease activity but can remove 3'-terminal chain-terminating residues from blocked DNA chains through a nucleotide-dependent mechanism leading to production of dinucleoside polyphosphates or through pyrophosphorolysis (the reversal of polymerization). The RT enzymes can be modified to enhance the desired cleavage activity as described in Meyer et al., Antimicrobial Agents and Chemotherapy, 44(12), 2000, p. 3465-3472 and Meyer et al., Proc. Natl. Acad. Sci., v95, pp. 13471-13476, 1998.

Exonuclease Activity

In some preferred aspects of the invention, the selective cleaving activity comprises an exonuclease activity. The exonuclease activity can be a polymerase-associated exonuclease activity or an autonomous exonuclease activity. Many DNA polymerases, for example, comprise a polymerase associated exonuclease activity, either as part of the same polynucleotide strand as the polymerase, or as an associating subunit. DNA polymerases are template-directed phosphoryl-transfer enzymes. They can synthesize long polymers of nucleoside monophosphates, the linear spatial disposition of which is dictated by the sequence of the complementary template DNA strand. The phosphoryl-transfer reaction at the heart of polymerization is catalysed by a two-metal-ion mechanism. Two $Mg^{2+}$ ions form a penta-coordinated transition state with the phosphate groups of the incoming nucleotide by interacting with conserved carboxylate residues in the active site of the enzyme. A common feature of polymerases is the concerted movement of the finger subdomains. These rotate towards the palm to switch from an 'open' to a 'closed' conformation, which forms the binding pocket for the incoming nucleotide or nucleotide analog.

Some DNA polymerases, for example pol δ and pol ε have catalytic subunits which contain a 3'-5' proofreading exonuclease domain at their amino terminus. In crystal structures, this domain is folded around a central-sheet—which contains the active site—and, together with the polymerase domain, creates a ring-shaped structure with a central hole in which the template—primer duplex DNA is positioned. The last nucleotide to be incorporated can be removed by the exonuclease activity using a two-metal-ion-catalysed phosphoryl transfer, which is analogous to the one that is responsible for polymerization. The 3'-5' exonuclease activity allows a polymerase to remove misincorporated nucleotides, and this ensures the high-fidelity DNA synthesis that is required for faithful replication. So, during DNA synthesis, pol δ and pol ε repetitively shuttle between 'polymerizing' and 'editing' modes, and the balance between these two activities is regulated by competition for the 3' end of the primer between the exonuclease and polymerase active sites. These different functional states are also reflected at the structural level. The duplex DNA occupies the same position adjacent to the thumb in either the editing or the polymerizing modes, whereas the 3' end is bound to the exonuclease or polymerase active sites, respectively. These two sites can be separated by more than 30 Å.

Examples of suitable polymerase-associated exonucleases include *E. coli* pol I and pol II, bacteriophage polymerases such as polymerases from T4, RB69, T7, and φ29, and eukaryotic pol δ, pol ε and pol γ. The exonuclease activity and structure of some polymerases has been well characterized. See, e.g. Beese et al., EMBO Journal, 10(1), 25-33, 1991, Brautigam et al., J. Mol. Biol., 277, 363-377, 1998, and Perez-Arnaiz et al., J. Mol. Biol., 391, 797-807, 2009. Examples of suitable autonomous eukaryotic exonucleases include TREX1, TREX2, Mre11, WRN, RAD1, RAD9, the apurinic/apyrimidinic endonuclease APE1 and VDJP. Autonomous exonucleases are described, for example in Shevlev et al., Nature Reviews: Molecular Cell Biology, 3, 1-12, 2002. In some cases, the autonomous activity can be supplied by an exonuclease component from a polymerase enzyme, e.g. by supplying the exonuclease subunit alone as an autonomous agent or, for example by supplying a polymerase having exonuclease activity where the polymerase activity has been disabled, for example by site selective mutation.

Thus, the removal of the 3' hydroxyl leaving group can be carried out by either an 'intramolecular' or an 'intermolecular' mechanism. In the case of intramolecular mechanism, the DNA growing strand terminus with moves between the polymerase and exonuclease active sites without the enzyme dissociating from the DNA. The intramolecular exonuclease activity has benefits in that it can utilize a highly processive polymerase enzyme. In some cases, the process will be faster for the intramolecular mechanism, since it is not required that the polymerase dissociate and re-engage for each incorporation. In addition, where an intramolecular mechanism is utilizes, the approach in which the polymerase enzyme is immobilized on the substrate can readily be used.

In some aspects the method incorporates an exonuclease that is temperature dependent. By using a temperature dependent exonuclease activity, one can control the rate of exonuclease activity during the sequencing reaction by varying the temperature. For example, an exonuclease can be used that cleaves at a higher temperature than the temperature at which the polymerase activity occurs. At the lower temperature, a nucleotide that is blocked from extension is incorporated. The temperature is then raised, allowing for the exonuclease cleavage. The temperature is then lowered again to allow the addition of another nucleotide. This temperature cycling thus controls the rate of sequential addition and exo cleavage. Signals which occur at the times consistent with the appropriate activity can be given more weight than signals which occur at times which are inconsistent with the activity.

It is generally desirable for the exonuclease not to bind the nucleotide analog directly, but to bind first to the polymerase active site and only to access the nucleotide analog after it is incorporated into the nascent strand. The relative binding of the nucleotide analog to the polymerase over the exonuclease can be raised, for example, by properly selecting the nucleotide analog and/or by modifying the polymerase enzyme. It is also desirable that the exo activity effectively removes the 3' hydroxyl leaving group, but that it does not continue to remove nucleotides from the nascent strand. The removal of these nucleotides can lead to errors in sequencing as a nucleotide analog corresponding to the removed nucleotide could be added, and incorrectly called as the next nucleotide in the template. Restricting the exonuclease activity to removing predominantly or substantially only the 3' hydroxyl leaving group can be accomplished by selecting the proper exonuclease activity, modifying the selectivity of the exonuclease activity by methods well known in the art, and by selecting the 3'-hydroxyl leaving group to be highly cleaved by the exonuclease activity.

Single Molecule Sequencing

The methods compositions and systems of the invention can be used for single molecule sequencing of nucleic acids. For sequencing processes that rely upon monitoring of the incorporation of nucleotides into growing nascent strands being synthesized by the complex, the progress of the reaction through these steps is of significant importance. In particular, for certain "real time" nucleotide incorporation monitoring processes, the detectability of the incorporation event is improved based upon the amount of time the nucleotide is incorporated into and retained within the synthesis complex during its ultimate incorporation into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, 2003, and Eid et al. Science, 323, 133-138, 2009, the full disclosures of which are incorporated herein by reference in their entirety for all purposes.

Figure 9:
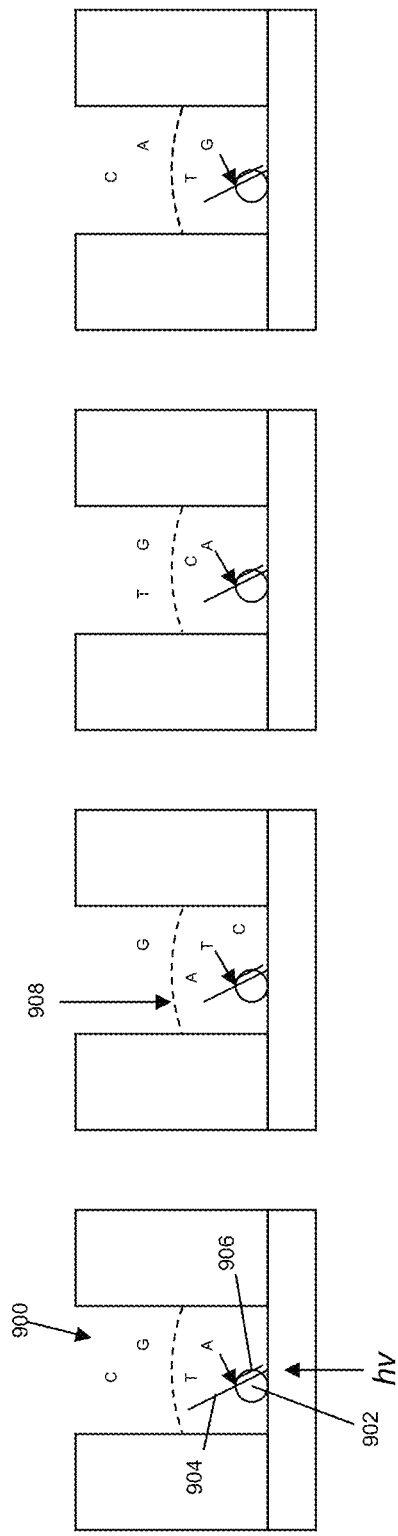
FIG. 9 shows a schematic illustration of performing sequencing within an optical confinement.

In an exemplary technique, as schematically illustrated in FIG. 9, a nucleic acid synthesis complex, including a polymerase enzyme 902, a template sequence 904 and a complementary primer sequence 906, is provided immobilized within an observation region 900, that permits illumination (as shown by hv) and observation of a small volume that includes the complex without excessive illumination of the surrounding volume (as illustrated by dashed line 908). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

In particularly preferred exemplary systems, the confined illumination volume is provided through the use of arrays of optically confined apertures termed zero mode waveguides, e.g., as shown by confined reaction region 900, (ZMWs) (See, e.g., U.S. Pat. No. 6,917,726, which is incorporated herein by reference in its entirety for all purposes). For sequencing applications, the DNA polymerase is provided immobilized upon the bottom of the ZMW (See, e.g., Korlach et al., PNAS U.S.A. 105(4): 1176-1181. (2008), which is incorporated herein by reference in its entirety for all purposes.

In operation, the fluorescently labeled nucleotides or nucleotide analogs (shown as A, C, G and T) bear one or more fluorescent dye groups on a terminal phosphate moiety that is cleaved from the nucleotide upon incorporation, and or one or more fluorescent dye groups whose removal by a selective cleaving activity will allow for further incorporation events. As a result of the cleavage and release of the labels, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al., Nucleosides, Nucleotides and Nucleic Acids, 27:1072:1083, 2008.

In another exemplary technique, the immobilized complex and the nucleotides to be incorporated are each provided with interactive labeling components. Upon incorporation, the nucleotide borne labeling component is brought into sufficient proximity to the complex-borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

Polymerase Mechanism

In natural polymerase mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation can be relatively complex. A diagrammatical representation of the incorporation biochemistry is provided in FIG. 10. This diagram is not a complete description of the mechanism of nucleotide incorporation. During the reaction process, the polymerase enzyme undergoes a series of conformational changes which can be essential steps in the mechanism.

Figure 10:
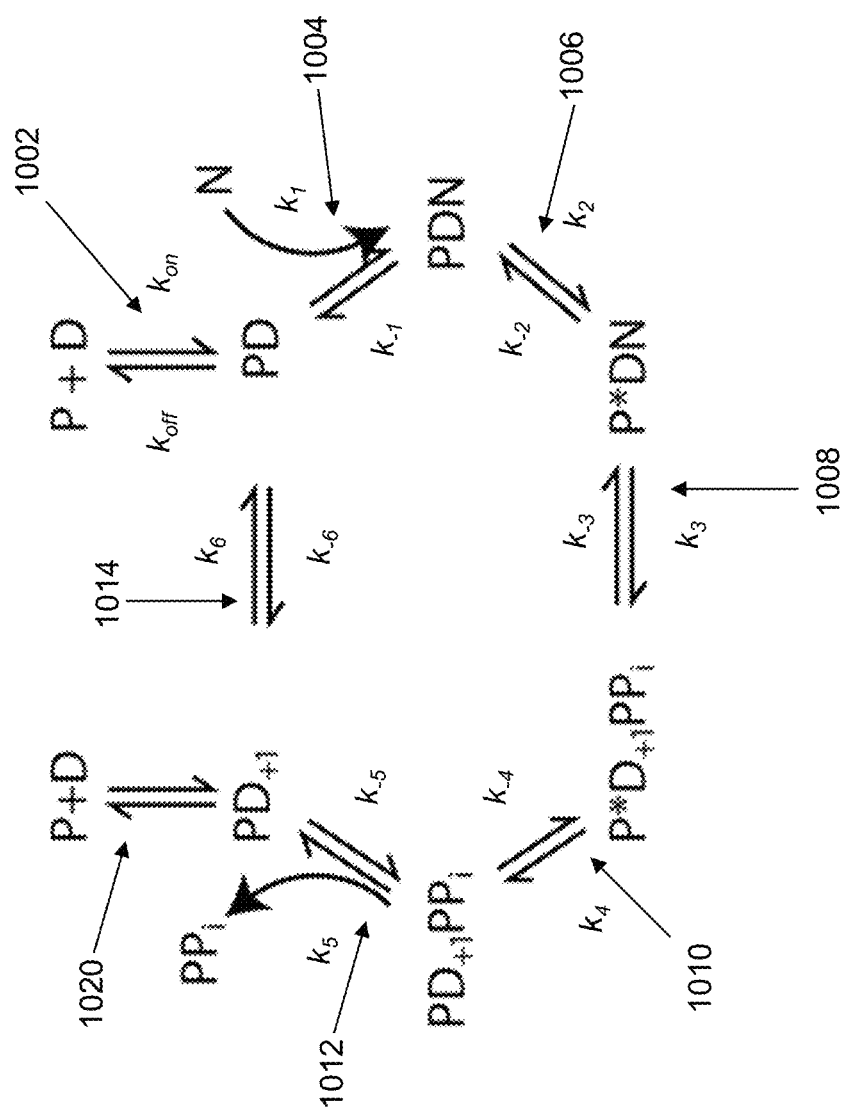
FIG. 10 shows the steps for a kinetic model for polymerase-mediated, template-directed nucleotide addition to a growing strand.

As shown in FIG. 10, the synthesis process begins with the binding of the primed nucleic acid template (D) to the polymerase (P) at step 1002. Nucleotide (N) binding with the complex occurs at step 1004. Step 1006 represents the isomerization of the polymerase from the open to closed conformation. Step 1008 is the chemistry step in which the nucleotide is incorporated into the growing strand. At step 1010, polymerase isomerization occurs from the closed to the open position. The polyphosphate component that is cleaved upon incorporation is released from the complex at step 1012. While the figure shows the release of pyrophosphate, it is understood that when a labeled nucleotide or nucleotide analog is used, the component released may be different than pyrophosphate. In many cases, the systems and methods of the invention use a nucleotide analog having a label on its terminal phosphate, such that the released component comprises a polyphosphate connected to a dye. With a natural nucleotide substrate, the polymerase then translocates on the template at step 1014. After translocation, the polymerase is in the position to add another nucleotide and continue around the reaction cycle.

In the methods of the present invention, a group that blocks further synthesis is removed by a selective cleaving activity to allow for continued synthesis. In some embodiments, the 3' hydroxyl leaving group blocks the addition of another nucleotide analog until the 3' hydroxyl leaving group is removed by the selective cleaving activity. Where the selective cleaving activity comprises an exonuclease activity, as describes above, the exonuclease activity may be polymerase-associated or from an autonomous exonuclease. Where the exonuclease activity is polymerase-associated, the cleavage of the 3' hydroxyl leaving group can take place without a dissociating step 1020 or 1002 taking place. The exonuclease acts to remove the 3' hydroxyl leaving group, thus enabling the growing strand to add another nucleotide analog and continue around the cycle. Where the exonuclease activity is autonomous, the polymerase must, in some cases, dissociate from the template and growing strand in order to allow the autonomous exonuclease activity to access the 3' hydroxyl leaving group. In such cases, the polymerase dissociates from the template-growing strand duplex in step 1002 or 1020, the autonomous exonuclease associates with the duplex, excises the 3' hydroxyl leaving group, the autonomous exonuclease dissociates, then a polymerase (generally a different polymerase molecule) associates with the template-growing strand in order to add the next nucleotide analog.

The use of a polymerase-associated exonuclease activity allows for the use of a processive polymerase. For a processive polymerase enzyme, the enzyme can add thousands or tens of thousands of nucleotides without dissociation. In many cases it is useful to use a polymerase enzyme which is processive for the real time sequencing of the invention.

As shown, the various steps can include reversible paths and may be characterized by the reaction constants shown in FIG. 10 where:

$k_{on}/k_{off}$=DNA binding/release;
$k_1/k_{-1}$=nucleotide binding/release;
$k_2/k_{-2}$=polymerase isomerization (open/closed);
$k_3/k_{-3}$=nucleotide incorporation (chemistry);
$k_4/k_{-4}$=polymerase isomerization (closed/open);
$k_5/k_{-5}$=polyphosphate release/binding;
$k_6/k_{-6}$=polymerase translocation.

Thus, during steps 1004 through 1010, the nucleotide is retained within the overall complex, and during steps 1004 and 1006, reversal of the reaction step will yield an unproductive event, i.e., not resulting in incorporation. For example, a bound nucleotide at step 1004, may be released regardless of whether it is the correct nucleotide for incorporation. Where the sequencing method comprises a nucleotide having a label which is released at step 1012, for example a nucleotide having a label on its terminal phosphate, the label is associated with the enzyme from step 1004 to step 1012. By observing the enzyme complex, we are able to detect the polyphosphate label while it is associated with the enzyme during these steps. For the methods of the invention, either alone or in addition to the label on the polyphosphate, the nucleotide analogs have a label on the 3' hydroxyl leaving group of the nucleotide analog. The 3' hydroxy leaving group label is present from the binding of the nucleotide analog at step 1004 through all of the steps of the cycle, until the selective cleaving activity removes the 3' hydroxyl leaving group. Once the polyphosphate is cleaved and the polyphosphate dissociates at step 1012, the reaction will very rarely proceed in the reverse direction. By observing both a label on the polyphosphate and a label on the 3'-hydroxyl leaving group, the actual incorporation of a nucleotide analog into the growing chain can be determined with greater confidence.

Interacting Labels—FRET

As described herein, in some embodiments, the polyphosphate label and the 3' hydroxyl leaving group label interact by FRET. Fluorescence resonance energy transfer, also termed Förster resonance energy transfer and abbreviated as FRET, generally comprises an energy transfer that occurs between two chromophores, namely, an energy donor and an energy acceptor as a result of absorption of excitation light by the energy donor. The energy transfer generally occurs through a coupled dipole-dipole interaction and a nonradiative transfer from donor to acceptor, without generation of an intermediate photon. The efficiency of energy transfer are strongly dependent on the separation distance between the donor and acceptor, such as varying by an inverse sixth power law, wherein the amount of energy transferred drops of at the $6^{th}$ power of the distance between the donor and acceptor. Accordingly, most FRET, for practical purposes, may be limited to a separation distance of less than about ten nanometers. Also, the efficiency of energy transfer is generally dependent on the spectral overlap of donor emission and acceptor absorption. After transfer of the energy from the donor to the acceptor, the acceptor can emit the energy transferred to it, generating a fluorescent signal with its characteristic fluorescent emission spectrum.

A FRET member or a member of a FRET pair generally comprises an energy donor or an energy acceptor of a donor-acceptor pair capable of FRET when in close proximity and with exposure to excitation light of a suitable wavelength. Accordingly, members of a FRET pair generally are or include a donor having an emission spectrum that overlaps the absorption spectrum of the acceptor.

In general, a fluorescent acceptor moiety should exhibit a good quantum yield and a large extinction coefficient; should be resistant to collisional quenching and bleaching; and should be easily conjugated to a variety of compositions and probe compositions by methods known to those having ordinary skill in the art. Suitable fluorophores include, without limitation, fluorescein, rhodamine, FITCs (e.g., fluorescein-5-isothiocyanate), 5-FAM, 6-FAM, 5,6-FAM, 7-hydroxycoumarin-3-carboxamide, 6-chloro-7-hydroxycoumarin-3-carboxamide, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid. Other suitable fluorophores include the Cy family of fluorophores (Cy 3, Cy3B, Cy3.5, Cy5; available from Amersham Biosciences, Piscataway, N.J.); the Alexa Fluor family (available from Molecular Probes, Eugene, Oreg.); the BODIPY family (available from Molecular Probes, Eugene, Oreg.); carbopyronins; squarines; cyanine/indocyanines; benzopyrylium heterocyles; and amide-bridged benzopyryliums.

The donor-acceptor pair may be described as a FRET pair. Exemplary FRET pairs may include fluorescein/rhodamine, Cy3/Cy5, lanthanide/phycobiliprotein, lanthanide/Cy5, cyan fluorescent protein (CFP)/yellow fluorescent protein (YFP), fluorescein/tetramethyrhodamine, 5-(2'-aminoethyl)-aminoapthalene-1-sulfonic acid (EDANS)/fluorescein and EDANS/DABCYL among others. Donor and acceptor molecules suitable for FRET are well known in the art (see R. P. Haugland, Handbook of Fluorescent Probes and Research Chemicals, 6th ed.; Molecular Probes, Oregon, the teachings of which are incorporated herein by reference).

In some embodiments, the donor fluorophore comprises Atto532 where the donor fluorophore comprises PB570 or Alexa568, providing a green FRET system for use with labeled nucleotides having a gap in their excitation spectra in this wavelength range, which uses, for example Alexa555, and Alexa594 or Biotium 052-125. In some cases, a red FRET system is used, for example using a 532 nm laser not excite analogs Alexa555-dT6P, PB570/Alexa568-dG6P, and Alexa594/Biotium052-125-dC6P; and a 643 nm laser to excite PB692-dA6P and a PB650 FRET donor, which transfers energy to the FRET acceptor A647.

Interacting Labels—Quenching

As described herein, in some embodiments, the polyphosphate label and the 3' hydroxyl leaving group label interact by quenching. As with FRET, quenching provided a signal which can be sensitive to changes in distance on the order of 0.1 nm to 10 nm. The donor-acceptor pair can be attached in any of the positions described herein with respect to FRET pairs. In some cases, the quenching may be part of a FRET process. FRET detection allows for the observation from the acceptor fluorophore, providing a signal which becomes higher in intensity as the donor and acceptor get closer together.

Any suitable quencher can be used. In some cases, a quenching molecule is a weakly fluorescent dye.

Suitable quenchers include dark quenchers, molecules which provide quenching of a donor fluorophore, but have little or no fluorescence of their own. Examples of quenchers include, but are not limited to DABCYL (4-(4'-dimethylaminophenylazo)benzoic acid) succinimidyl ester, diarylrhodamine carboxylic acid, succinimidyl ester (QSY-7), and 4',5'-dinitrofluorescein carboxylic acid, succinimidyl ester (QSY-33) (all available from Molecular Probes), IRDye QC-1 from Li-Cor Biosciences, and quenchers Redmond Red™, Yakima Yellow™, and Eclipse™ available from Epoch or Glen Biosciences. Suitable quenchers include black hole quenchers such as BHQ1, BHQ3, and BHQ2 and other quenchers as described on the Biosearch Technologies website.

Polymerase Enzymes

Polymerase enzymes having labels indicative of polymer conformation can include polymerases mutated to have desirable properties for sequencing. For example, suitable enzymes include those taught in, e.g., WO 2007/076057, WO 2008/051530, and U.S. patent application Ser. No. 12/584,481 filed Sep. 4, 2009. The modified polymerases may have modified properties such as (e.g., decreased branch fraction formation, improved specificity, improved processivity, altered rates, improved retention time, improved stability of the closed complex, etc.).

In addition, the polymerases can be further modified for application-specific reasons, such as to increase photostability, e.g., as taught in U.S. patent application Ser. No. 12/384,110 filed Mar. 30, 2009, to improve activity of the enzyme when bound to a surface, as taught, e.g., in WO 2007/075987, and WO 2007/076057, or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

DNA Polymerases

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2 (1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584, 481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or U.S. Pat. No. 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287.

RNA Polymerases

In some embodiments, the polymerase enzyme that is used for sequencing is an RNA polymerase. Any suitable RNA polymerase can be used including RNA polymerases from bacteria, eukaryotes, viruses, or archea. Suitable RNA polymerases include RNA PoI I, RNA PoI II, RNA PoI III, RNA PoI IV, RNA PoI V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors.

There are many proteins that can bind to RNAP and modify its behavior. For instance, GreA and GreB from *E. coli* and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e. they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or systems of the invention include RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Reaction Conditions

The reaction conditions used can influence the relative rates of the various reactions. Thus, controlling the reaction conditions can be useful in ensuring that the sequencing method is successful at calling the bases within the template at a high rate. The reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance two slow step behavior of polymerases is described in detail in U.S. patent application Ser. No. 12/414,191 filed Mar. 30, 2009, and entitled "Two slow-step polymerase enzyme systems and methods."

Enzymatic reactions are often run in the presence of a buffer, which is used, in part, to control the pH of the reaction mixture. The type of buffer can in some cases influence the kinetics of the polymerase reaction in a way that can lead to two slow-step kinetics. For example, in some cases, use of TRIS as buffer is useful for obtaining a two slow-step reaction. Suitable buffers include, for example, TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two slow-step kinetics. The pH can be adjusted to a value that produces a two slow-step reaction mechanism. The pH is generally between about 6 and about 9. In some cases, the pH is between about 6.5 and about 8.0. In some cases, the pH is between about 6.5 and 7.5. In some cases, the pH is about 6.5, 6.6, 6.7, 6.8, 6.9, 7.0, 7.1, 7.2, 7.3, 7.4, or 7.5.

The temperature of the reaction can be adjusted to ensure that the relative rates of the reactions are occurring in the appropriate range. The reaction temperature may depend upon the type of polymerase or selective cleaving activity such as econuclease which is employed. Temperatures between 15° C. and 90° C., between 20° C. and 50° C., between 20° C. and 40° C., or between 20° C. and 30° C. can be used.

In some cases, additives can be added to the reaction mixture that will influence the kinetics of the reaction. In some cases, the additives can interact with the active site of the enzyme, acting for example as competitive inhibitors. In some cases, additives can interact with portions of the enzyme away from the active site in a manner that will influence the kinetics of the reaction. Additives that can influence the kinetics include, for example, competitive but otherwise unreactive substrates or inhibitors in analytical reactions to modulate the rate of reaction as described in copending U.S. Utility patent application Ser. No. 12/370,472, the full disclosure of which is incorporated herein by reference in its entirety for all purposes.

As another example, an isotope such as deuterium can be added to influence the rate of one or more step in the polymerase reaction. In some cases, deuterium can be used to slow one or more steps in the polymerase reaction due to the deuterium isotope effect. By altering the kinetics of steps of the polymerase reaction, in some instances two slow step kinetics, as described herein, can be achieved. The deuterium isotope effect can be used, for example, to control the rate of incorporation of nucleotide, e.g., by slowing the incorporation rate. Isotopes other than deuterium can also be employed, for example, isotopes of carbon (e.g. $^{13}C$), nitrogen, oxygen, sulfur, or phosphorous.

As yet another example, additives that can be used to control the kinetics of the polymerase reaction include the addition of organic solvents. The solvent additives are generally water soluble organic solvents. The solvents need not be soluble at all concentrations, but are generally soluble at the amounts used to control the kinetics of the polymerase reaction. While not being bound by theory, it is believed that the solvents can influence the three dimensional conformation of the polymerase enzyme which can affect the rates of the various steps in the polymerase reaction. For example, the solvents can affect steps involving conformational changes such as the isomerization steps. Added solvents can also affect, and in some cases slow, the translocation step. In some cases, the solvents act by influencing hydrogen bonding interactions.

The water miscible organic solvents that can be used to control the rates of one or more steps of the polymerase reaction in single molecule sequencing include, e.g., alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents also include small molecule ethers such as tetrahydrofuran (THF) and dioxane, dimethylacetamide (DMA), dimethylsulfoxide (DMSO), dimethylformamide (DMF), and acetonitrile.

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

One aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interaction in polymerase reactions, see, e.g., Arndt, et al., Biochemistry (2001) 40:5368-5375. Suitable conditions include those described in U.S. patent application Ser. No. 12/384,112 filed Mar. 30, 2009.

Template Nucleic Acids

The template nucleic acids of the invention can comprise any suitable polynucleotide, including double-stranded DNA, single-stranded DNA, single-stranded DNA hairpins, DNA/RNA hybrids, RNAs with a recognition site for binding of the polymerizing agent, and RNA hairpins. Further, target polynucleotides may be a specific portion of a genome of a cell, such as an intron, regulatory region, allele, variant or mutation; the whole genome; or any portion thereof. In other embodiments, the target polynucleotides may be mRNA, tRNA, rRNA, ribozymes, antisense RNA or RNAi. The target polynucleotide may be of any length, such as at between about 10 bases and about 100,000 bases, or between about 100 bases and 10,000 bases.

The template nucleic acids of the invention can include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. A nucleic acid can be e.g., single-stranded or double-stranded.

Nucleotide Analogs

The nucleotide analogs for use in the invention can be any suitable nucleotide analog that is capable of being a substrate for the polymerase and for the selective cleaving activity. It has been shown that nucleotides can be modified and still used as substrates for polymerases and other enzymes. Where a variant of a nucleotide analog is contemplated, the compatibility of the nucleotide analog with the polymerase or with another enzyme activity such as exonuclease activity can be determined by activity assays. The carrying out of activity assays is straightforward and well known in the art.

The nucleotide analogs of the invention generally comprise a substituent that blocks the 3' hydroxyl of the nucleotide analog from further extension of the growing nucleic acid chain after the nucleotide analog is incorporated. The blocking substituent is capable of being removed by a selective cleaving agent to unblock the 3' hydroxyl and allow the incorporation of another nucleotide analog. In some embodiments the substituent is covalently linked to the oxygen of the 3' hydroxyl of the nucleotide analog, comprising a leaving group which is removed by the selective cleaving agent. In some embodiments the substituent is not attached to the oxygen of the 3' hydroxyl, but is attached to another portion of the nucleotide analog such as the base, and extends from the base in a manner that blocks nucleotide additions until it is removed. The blocking substituent comprises a label that is released upon cleavage of the blocking substituent.

One aspect of the invention is a nucleotide analog that has two cleavable labels. The two cleavable labels are each cleavable in separate chemical steps, one or both of which may be an enzymatic step. For example in some embodiments, one of the labels is cleaved by a polymerase upon incorporation into a growing nucleic acid strand, and the other label is cleaved by second enzyme to unblock the 3' hydroxyl of the nucleotide analog to allow the addition of a further nucleotide analog to the growing chain. The second enzyme can be, for example a phosphatase, esterase, or exonuclease. The labels are attached in a manner such that the nucleotide analog can act as a substrate for the polymerase and the selective cleavage activity enzyme.

The nucleotide analog can be, for example, a nucleoside polyphosphate having three or more phosphates in its polyphosphate chain with a label on the portion of the polyphosphate chain that is cleaved upon incorporation into the growing strand, the nucleoside polyphosphate also having a label on a 3' hydroxyl leaving group. The labeled leaving group on the 3' hydroxyl is subsequently cleaved by an enzyme such as an exonuclease. The polyphosphate can be a pure polyphosphate, e.g. —O—PO3-, or the polyphosphate can include substitutions. For example, one or more of the linking oxygens in the polyphosphate can comprise an S, an NH or an NR group, where R is a substituted or unsubstituted alkyl group. R can act as a place on the polyphosphate for including functionality for improved binding of the nucleotide, or can provide a place for attaching a label, with or without a linker.

In some embodiments, the labeled 3' hydroxyl leaving group on the nucleotide analog comprises a labeled nucleoside monophosphate attached to the 3' hydroxyl of the nucleotide analog. The labeled nucleoside monophosphate generally has its 3' hydroxyl position blocked to prevent extension of the growing strand from this position. The label can be attached to any suitable position on the nucleoside monophosphate, for example attached to the 3' hydroxyl or attached to the nucleobase of the nucleoside monophosphate. With a nucleoside monophosphate attached to its 3' hydroxyl, the nucleotide analog becomes a dinucleotide polyphosphate. In some cases, the nucleoside monophosphate comprises a dideoxy nucleoside monophosphate. The dinucleotide polyphosphates of the invention can be prepared using methods known for the synthesis of dinucleotide phosphates. See, for example, Zhong et al. Antimicrobial Agents and Chemotherapy, 47 (8), p 2674 (2003), Lebedev et al. Nucleosides, Nucleotides and Nucleic Acids, 20 (4-7), 1403-1409, 2001, Abramova et al. Bioinorganic and Medicinal Chemistry, 15, 6549-6555, 2007, and Abramova et al. Bioinorganic and Medicinal Chemistry, 16, 9127-9132, 2008.

In order for the nucleotide analogs of the invention to be used for sequencing, the nucleotide analog having the labeled 3' hydroxyl leaving group is a substrate for the polymerase enzyme, and the incorporated nucleotide analog is a substrate for the selective cleaving activity, for example the exonuclease activity. It has been shown that nucleotides modified at the 3' position can act as substrates for polymerase enzymes. See e.g. Wu et al. PNAS, 104(42), 16462 (2007).

In addition, the methods for modifying the properties of enzymes such as polymerases have improved in recent years, allowing the modification of the polymerase and/or the exonuclease in order for it to act on the non-natural nucleotide analogs.

In one aspect, the invention provides a composition comprising a compound of Formula I or Formula II.

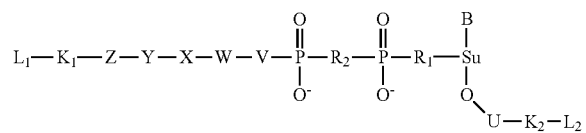

Formula I

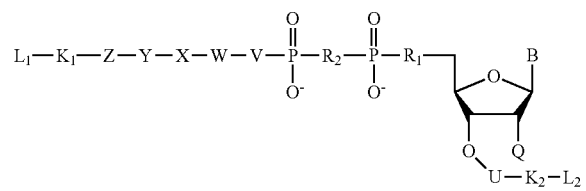

Formula II wherein B is a nucleobase; Su is a sugar, acyclic moiety or carbocyclic moiety; Q is H, OH, SH, or NHR; $R_1$ is selected from O and S; $R_2$ is selected from O, NH, NR, S, $CH_2$, CRR', $CH_2CH_2$, CRR'CRR', C(O), CRNHR'; R and R' are independently selected from H, F, Cl, OH, $NH_2$, methyl, ethyl, propyl, $C_2$-$C_6$ alkyl, $C_2$-$C_6$ alkenyl, $C_2$-$C_6$ alkynyl, aryl, heterocycle, 4-pyridine, and 1-imidazone; V, W, X, Y, and Z are each independently selected from a single bond, or

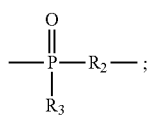

U is a single bond,

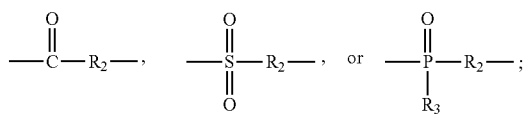

$R_3$ is selected from —OR, —SR, —NRR', or —$CH_2R$; $K_1$ and $K_2$ are linker moieties; and $L_1$ and $L_2$ are detectable labels.

In some embodiments the $R_2$ in each portion of the compound is independently selected from O, NH, S, methylene, $CHNH_2$, $CH_2CH_2$, $C(OH)CH_2R$.

The nucleobase moiety comprises natural or non-natural nucleobases or nucleobase analogs, including, e.g., purine or pyrimidine bases that are routinely found in nucleic acids and nucleotide analogs, including adenine, thymine, guanine, cytidine, uracil, and in some cases, inosine. The nucleobases are generally chosen to act as nucleotides and nucleotide analogs, for example in enzymatic reactions such as polymerase synthesis of nucleic acids. The nucleotide analogs comprising such nucleobases are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion.

In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

The linkers, e.g. $K_1$ and $K_2$ can be any suitable linker. The linkers generally provide space between the core molecule and the linker. In some cases, the linkers can affect the position and mobility of the label with respect to the core molecule. In some cases, the linker can provide solubility, or provide the appropriate polarity, H-bonding, or ionic characteristics for optimal binding of the nucleotide analog to the polymerase enzyme or interaction with the endogenous cleaving activity such as an exonuclease or exonuclease domain. For the present invention, the linker should generally not inhibit the acceptance of the nucleotide analog by a polymerase or exonuclease. A wide variety of linkers and linker chemistries are known in the art of synthetic chemistry may be employed in coupling the labeling group to the analogs of the invention. For example, such linkers may include organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In preferred aspects, alkyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes.

In some cases, adjustable length linking groups are used to provide linkage of the labeling group to the rest of the compound, such as alkyl, aryl, peptidyl, or oligonucleotide based linkages. For example, in certain preferred aspects, methyl, ethyl, butyl, propyl, pentyl, hexyl, or longer chain alkyl groups are employed. The linker groups may be coupled through any conventional linkage technique, including, for example, an amide linkage generated through standard NHS chemistry.

The linkers may independently comprise single bonds, single atoms or larger molecules. For example $K_1$ and $K_2$ may be independently selected from O, N, S, or the like, or they may include larger structures, such as alkyl, aminoalkyl, alkoxyl, aryl, polyaryl, or multimeric linker groups, such as or other larger linkages. Multimeric linkages are also envisioned as linking groups for one or both of $K_1$ and $K_2$, including, e.g., vinyl groups, nucleic acid linkers, peptidyl linkers, polyethylene glycol linkers, polybenzyl or other polyaryl groups, or other appropriate linkages. In some aspects, the linking groups $K_1$ and $K_2$ will be independently selected from individual atoms, such as O, N or S, alkyl groups of from 1 to 18 carbons in length, including substituted alkyl groups, such as aminoalkyl linkers. Optionally, alkoxy groups of from 1 to 18 carbons are employed as linkers. In certain exemplary embodiments, aminohexyl groups are employed as linkers alone or in conjunction with longer alkoxy groups, such as aminohexyl-aminoheptanoic acid linkers or the like. Suitable linkers are described in U.S. Patent Application 2009/0246791 filed Mar. 26, 2009, and 2009/0325260 filed Feb. 6, 2009 which are incorporated by reference herein for all purposes. In some embodiments the linker $K_2$ comprises a structure of Formula III.

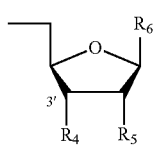

Formula III wherein $R_4$ and $R_5$, are independently selected from a bond to L2, H, OH, $OR_7$, $SR_7$ or $NHR_7$; $R_7$ is H, methyl or a $C_2$-$C_6$ alkyl group; and $R_6$ is either a bond to $L_2$, a nucleobase, or an aryl, heteroaryl, or $C_1$-$C_6$ aliphatic moiety.

The labeling groups $L_1$ and $L_2$ are typically a readily detectable labeling group, such as a luminescent, fluorescent, fluorogenic, chromogenic, magnetic, radioactive or other type of detectable label. In preferred aspects, the labeling groups $L_1$ and $L_2$ are selected from fluorescent labeling groups including individual fluorophores and cooperative fluorophores, e.g., one or both members of a donor-quencher or a FRET pair. In the case in which $L_1$ or $L_2$ is at least one member of a cooperative fluorophore pair, the second member of the pair may also be included within the same $L_1$ or $L_2$ group, e.g., as a unified FRET dye structure (See, e.g., U.S. Pat. No. 5,688,648 for a discussion of FRET dyes), or it may be provided elsewhere on the analog or the overall system. For example, L1 is the donor and L2 is the acceptor, or L2 is the donor and L1 is the receptor. In some cases, the other member of the pair may be coupled to and as a portion of the nucleobase moiety attached to the sugar group (See, e.g., U.S. Pat. No. 6,232,075 previously incorporated herein by reference). Alternatively, the other member of the pair may be coupled to another reaction component, e.g., a polymerase enzyme (See, e.g., U.S. Pat. No. 7,056,676, previously incorporated herein by reference).

The term "aryl" refers to phenyl or naphthyl which may be optionally substituted. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

A group is "substituted" if it has a substituent that is, for example, one of the groups: OR, NHR, $NR_2$, SR, $CRH_2$, CHRR', $CH_2CH_3$, CRR'CHRR', C(O), CHRNHR', where R and R' are independently selected from H, F, Cl, OH, $NH_2$, methyl, ethyl, propyl, $C_2$-$C_6$ alkyl, $C_2$-$C_6$ alkenyl aryl, heterocycle, 4-pyridine, and 1-imidazone.

A wide variety of different types of fluorophores are readily available and applicable to the compounds of the invention and include fluorescein, or rhodamine based dyes, cyanine dyes and the like. A variety of such dyes are commercially available and include the Cy dyes available from GE Healthcare (Piscataway, N.J.), such as Cy3, Cy5, and the like, or the Alexa® family of dyes available from Invitrogen/Molecular Probes (Carlsbad, Calif.), such as Alexa 488, 500, 514, 532, 546, 555, 568, 594, 610, 633, 647, 660, 680, 700, and 750. These fluorophores may be present as individual fluorophores or they may be present in interactive pairs or groups, e.g., as fluorescent resonant energy transfer (FRET) pairs.

The terms "heteroaryl" refer to a substituted or unsubstituted 5- or 6-membered unsaturated ring containing one, two, three, or four independently selected heteroatoms, preferably one or two heteroatoms independently selected from oxygen, nitrogen, and sulfur or to a bicyclic unsaturated ring system containing up to 10 atoms including at least one heteroatom selected from oxygen, nitrogen, and sulfur. Examples of hetaryls include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. The heterocyclic ring may be optionally substituted with one or more substituents. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc. and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Additional details regarding analogs and methods of making such analogs can be found in U.S. patent application Ser. No. 11/241,809, filed Sep. 29, 2005, and incorporated herein by reference in its entirety for all purposes.

Alternative labeling strategies may employ inorganic materials as labeling moieties, such as fluorescent or luminescent nanoparticles, e.g. nanocrystals, i.e. Quantum Dots, that possess inherent fluorescent capabilities due to their semiconductor make up and size in the nanoscale regime (See, e.g., U.S. Pat. Nos. 6,861,155, 6,699,723, 7,235,361, which are incorporated by reference herein for all purposes).

Such nanocrystal materials are generally commercially available from, e.g., Invitrogen, Inc., (Carlsbad Calif.). Again, such compounds may be present as individual labeling groups or as interactive groups or pairs, e.g., with other inorganic nanocrystals or organic fluorophores. In some cases fluorescent proteins can be used such as green fluorescent protein (GFP, EGFP), blue fluorescent protein (EBFP, EBFP2, Azurite, mKalama1), cyan fluorescent protein (ECFP, Cerulean, CyPet) and yellow fluorescent protein derivatives (YFP, Citrine, Venus, YPet).

In some cases labels that are not optical labels can be used, such as spin labels, magnetic labels. By using non-optical labels, a signal is obtained with is orthogonal to the optical signal. Non-optical labels for some of the labels in the system allows for the optical labels to have more spectral space.

In some aspects the invention comprises a composition having a compound of the structure of Formula IV.

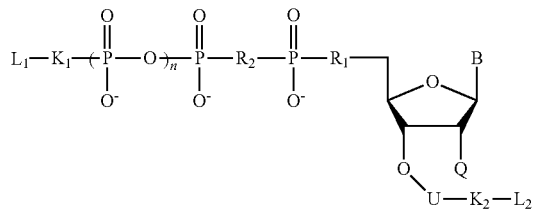

Formula IV wherein B is a nucleobase; Q is H, OH, SH, or NHR; $R_1$ is selected from O and S; $R_2$ is selected from O, NH, NR, S, $CH_2$, CRR', CH2CH2, CRR'CRR', C(O), CRNHR'; R and R' are independently selected from H, F, Cl, OH, NH2, methyl, ethyl, propyl, $C_2$-$C_6$ alkyl, $C_2$-$C_6$ alkenyl, $C_2$-$C_6$ alkynyl, aryl, heterocycle, 4-pyridine, and 1-imidazone; U is a single bond,

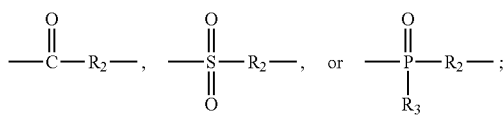

$R_3$ is selected from —OR, —SR, —NRR', or —$CH_2R$; $K_1$ and $K_2$ are linker moieties; $L_1$ and $L_2$ are detectable labels; and n is from 0 to 6.

In some embodiments the linker $K_2$ comprises a structure of Formula III.

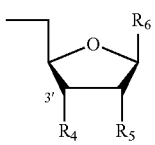

Formula III wherein $R_4$ and $R_5$ are independently selected from a bond to L2, H, OH, $OR_7$, $SR_7$ or $NHR_7$; $R_7$ is H, methyl or a $C_2$-$C_6$ alkyl group and $R_6$ is either a bond to $L_2$, a nucleobase, or an aryl, heteroaryl, or $C_1$-$C_6$ aliphatic moiety.

In some embodiments the invention comprises a composition comprising a compound of Formula IV, wherein B is a nucleobase which comprises A, G, C, T, or U; wherein Q is H or OH, wherein $R_1$ and $R_2$ are independently selected from O and S; wherein n is from 1 to 4; $K_1$ and $K_2$ are linker moieties and where $L_1$ and $L_2$ comprise fluorescent dyes.

In some aspects, the invention comprises a composition comprising a compound of Formula V.

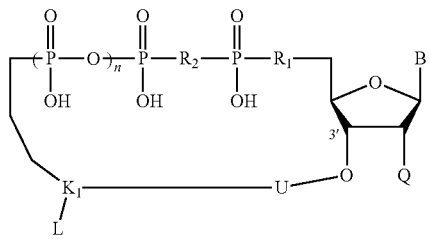

Formula V wherein B is a nucleobase; Q is H, OH, SH, or NHR; $R_1$ is selected from O and S; $R_2$ is selected from 0, NH, NR, S, $CH_2$, CRR', CH2CH2, CRR'CRR', C(O), CRNHR'; R and R' are independently selected from H, F, Cl, OH, NH2, methyl, ethyl, propyl, $C_2$-$C_6$ alkyl, $C_2$-$C_6$ alkenyl, $C_2$-$C_6$ alkynyl, aryl, heterocycle, 4-pyridine, and 1-imidazone; U is a single bond,

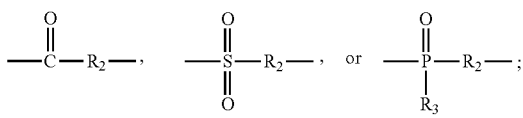

$R_3$ is selected from —OR, —SR, —NRR', or —$CH_2R$; $K_1$ is a linker moiety; L is a detectable label; and n is from 0 to 6.

The analogs of the invention can be synthesized by methods known in the art, and many non-natural nucleotides have been shown to be incorporated by polymerases. See e.g. Wolf, Nucleic Acids Research, 30(17), 3739-3747 (2002), Finn et al. Nucleic Acids Research, 31(16), 4769 (2003), Cook et al., J. Am. Chem. Soc., 91(23), 6479-6484, 1969, Hoard et al., J. Am. Chem. Soc., 87(8), 1785-1788, 1965, Abramova et al., Tett. Lett. 45, 4361-4364, 2004.

Systems

The invention includes systems for sequencing of nucleic acid templates. The systems provide for concurrently sequencing a plurality of nucleic acid templates. The system can incorporate all of the reagents and methods described herein, and provides the instrumentation required for containing the sample, illuminating the sample with excitation light, detecting light emitted from the sample during sequencing to produce intensity versus time data from the labeled nucleotides and from the label indicative of enzyme conformation, and determining the sequence of a template using the intensity versus time data.

The system for sequencing generally comprises a substrate having a plurality of single polymerase enzymes, single templates, or single primers bound to the surface. In the case of a highly processive enzyme polymerase complexes each comprising a polymerase enzyme, a nucleic acid template, and a primer are immobilized. The sequencing reagents generally include two or more types of nucleotide analogs, each nucleotide analog labeled with a different label. The polymerase sequentially adds nucleotides or nucleotide analogs to the growing strand, which extends from the primer. Each added nucleotide or nucleotide analog is complementary to the corresponding base on the template nucleic acid, such that the portion of the growing strand that is produced is complementary to the template.

The system comprises illumination optics for illuminating the enzyme complexes. The illumination optics illuminate the complexes in a wavelength range that will excite the labels on the nucleotides or nucleotide analog and which will excite the labels on the polymerase enzyme that are sensitive to changes in conformation.

The system further comprises detection optics for observing signals from the labeled nucleotides or nucleotide analogs and signals from the labeled enzyme during the enzyme mediated addition. The detection optics observe a plurality of single polymerase enzyme complexes concurrently, observing the nucleotide or nucleotide analog additions for each of them. For each of the observed polymerase enzyme complexes, the detection optics concurrently observe the signals from each of the labeled nucleotides or nucleotide analogs and the signals from the labeled enzyme that are indicative of enzyme conformation.

The system also comprise a computer configured to determine the type of the nucleotides or nucleotide analog that is added to the growing strand using the observed signal from the label of the nucleotide or nucleotide analogs; whereby observed signals from the labeled polymerase enzyme are used to indicate whether a type of nucleotide or nucleotide analog is incorporated into the growing strand. The computer generally receives information regarding the observed signals from the detection optics in the form of signal data. The computer stores, processes, and interprets the signal data, using the signal data in order to produce a sequence of base calls. The base calls represent the computers estimate of the sequence of the template from the signal data received combined with other information given to the computer to assist in the sequence determination.

Figure 11:
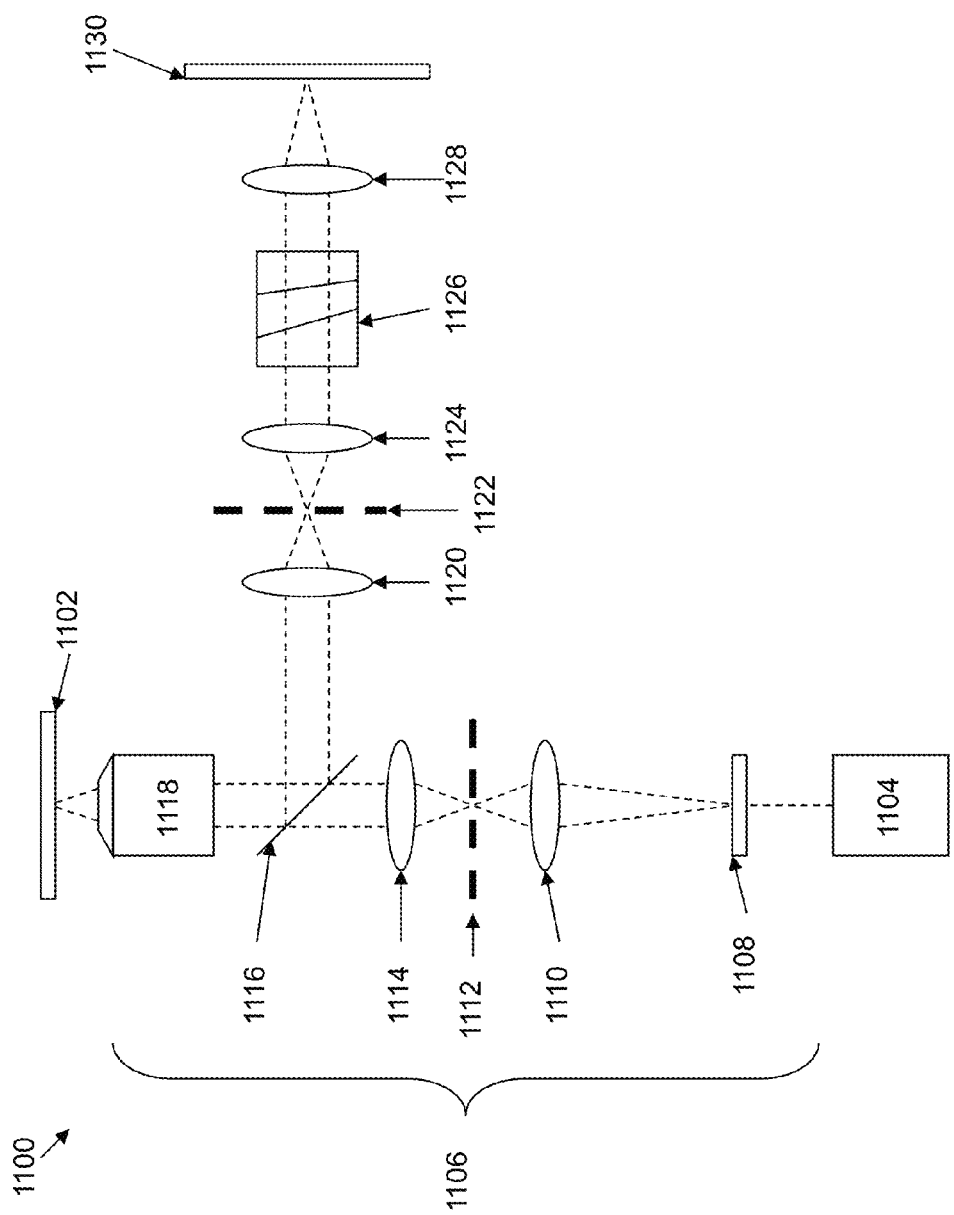
FIG. 11 shows an embodiment of a system of the invention for carrying out single molecule sequencing.

One example of such system is illustrated in FIG. 11. As shown, the system 1100, includes a reaction array, such as a zero-mode waveguide array 1102 upon which a number of discrete reaction regions are arrayed. Within the zero-mode waveguides are immobilized single polymerase enzyme complexes, single templates or single primers having labels indicative of enzyme conformation. The zero-mode waveguides are also exposed to sequencing reagents including labeled nucleotides or nucleotide analogs, for example four differentially labeled nucleotides or nucleotide analogs. In the case of a zero mode waveguide array, large numbers of zero mode waveguides are typically provided arrayed in rows and columns on the substrate. Within the various ZMWs are provided reactants of interest for a given analysis. For example, in the context of nucleic acid sequencing by synthesis, a sequencing complex that includes a template nucleic acid sequence, a complementary primer sequence, a nucleic acid polymerase enzyme, and a reaction mixture of nucleotide analogs required for primer extension are provided with the ZMW. ZMW arrays can be fabricated at ultra high density, providing anywhere from 1100 ZMWs per $cm^2$, to 1,000,000 ZMWs per $cm^2$, or more. Thus, at any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate.

As shown in FIG. 11, the system includes a source of excitation radiation for exciting fluorescent reactants in the reaction regions, such as laser 1104. An optical train 1106 delivers excitation radiation from laser 1104 to the ZMW array or substrate 1102. The optical train also collects fluorescent signals from the various ZMWs on the array, and conveys those signals to a detector, such as EMCCD 1130. The optical train 1106 includes a multiplex component, such as diffractive optical element (DOE) 1108 (also referred to as a holographic optical element or HOE), that converts a single excitation beam to large number of discrete excitation beams that will be targeted in an array of illumination spots that correspond to the location of the ZMWs on the array 1102. The multiple beams are passed through a dichroic 1116 that is selected to pass excitation light and reflect the fluorescence from the array 1102. Prior to passing through the dichroic 1116, the illumination beams may be passed through a confocal filter 1112 which may have associated with it a pair of focusing lenses, e.g., lenses 1110 and 1114, in order to focus these beams through the confocal pinhole (s). The excitation light that is passed through dichroic 1116 is then focused in a targeted pattern onto the plane of the array 1102 via objective lens 1118.

Fluorescent signals from array 1102 are then collected by the objective lens 1118, and passed to dichroic 1116, which reflects the fluorescent signals toward detector 1130. The signals from the discrete ZMWs on the array are then passed through a spatial filter, such as confocal mask 1122, to reduce background noise, such as photoluminescence, out of focal plane autofluorescence or scattered light, which again typically has associated with it a pair of focusing lenses, e.g., lenses 1120 and 1124. The signals can then be passed through a dispersive optical element, such as wedge prism 1126, that differentially directs light of differing spectral characteristics, allowing for distinction of different fluorescent signals based upon the location upon the detector, upon which they impinge. The differentially directed signal components are then directed through additional focusing optics, e.g., focusing lens 1128, and ultimately impact the EMCCD detector 1130. As noted, the position on the detector upon which a given signal is incident can then be indicative of (1) the originating ZMW in the array, and (2) the spectral characteristics of the signal component, which is used, for example, to identify the type of fluorescently labeled nucleotide analog incorporated in an extension reaction and that is used to monitor the label on the enzyme which is indicative of enzyme conformation.

Optical illumination and detections systems which can be used with the present invention are described, for example in U.S. patent application Ser. No. 12/351,173 filed Jan. 9, 2009, U.S. patent application Ser. No. 11/901,273 filed Sep. 14, 2007, U.S. patent application Ser. No. 12/151,979 filed May 9, 2008, U.S. patent application Ser. No. 12/079,944 filed Mar. 27, 2008, and U.S. patent application Ser. No. 11/849,157 filed Aug. 31, 2007, which are incorporated herein by reference for all purposes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

Optical Confinements—Zero-Mode Waveguides

In some embodiments of the methods and systems of the invention, optical confinements are used to enhance the ability to concurrently observe multiple single polymerase enzyme complexes simultaneously. In general, optical confinements are disposed upon a substrate and used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide illumination to or derive emitted radiation from only very small volumes. Examples of such optical confinements include systems that utilize, e.g., total internal reflection (TIR) based optical systems whereby light is directed through a transparent portion of the substrate at an angle that yields total internal reflection within the substrate.

The substrates of the invention are generally rigid, and often planar, but need not be either. Where the substrate comprises an array of optical confinements, the substrate will generally be of a size and shape that can interface with optical instrumentation to allow for the illumination and for the measurement of light from the optical confinements. Typically, the substrate will also be configured to be held in contact with liquid media, for instance containing reagents and substrates and/or labeled components for optical measurements.

Where the substrates comprise arrays of optical confinements, the arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is sometimes preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements, e.g., zero mode waveguides, are provided in arrays of more than 100, more than 1000, more than 10,000, more that 100,000, or more than 1,000,000 separate waveguides on a single substrate. In addition, the waveguide arrays typically comprise a relatively high density of waveguides on the surface of the substrate. Such high density typically includes waveguides present at a density of greater than 10 zero mode waveguides per $mm^2$, preferably, greater than 100 waveguides per $mm^2$ of substrate surface area, and more preferably, greater than 500 or even 1000 waveguides per $mm^2$ and in many cases up to or greater than 100,000 waveguides per mm $mm^2$. Although in many cases, the waveguides in the array are spaced in a regular pattern, e.g., in 2, 5, 10, 25, 50 or 100 or more rows and/or columns of regularly spaced waveguides in a given array, in certain preferred cases, there are advantages to providing the organization of waveguides in an array deviating from a standard row and/or column format. In preferred aspects, the substrates include zero mode waveguides as the optical confinements to define the discrete reaction regions on the substrate.

The optical confinements can be zero-mode-waveguides. Zero mode waveguides have been described in, e.g., U.S. Pat. No. 6,917,726, the full disclosure of which is incorporated herein by reference in its entirety for all purposes. Generally, such waveguides comprise a core disposed through a cladding layer, which in the case of applications to reactions, comprises an aperture disposed through the cladding layer that can receive the reactants to be monitored. Typically, the aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the core. In the case of optical signals (and excitation radiation), the waveguide cores will typically be between about 1 nm and about 300 nm, between about 10 and about 200 nm, or between about 50 and about 150 nm in diameter where light in the visible range is used.

The overall size of the array of optical confinements can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

The individual confinement in the array can provide an effective observation volume less than about 1000 zeptoliters, less than about 900, less than about 200, less than about 80, less than about 10 zeptoliters. Where desired, an effective observation volume less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar ($\mu M$), or more preferably higher than 50 $\mu M$, or even higher than 100 $\mu M$.

As zero-mode-waveguide can provide an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single-molecules, even when they are present at a concentration as high as in the micromolar range.

The zero-mode-waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation that is opaque and/or reflective materials. Suitable materials for fabricating the cladding include but are not limited to metals, metal oxides, alloys, and semi-conducting materials, and any combination thereof.

The internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda c$). For a circular guide of diameter d and having a clad of perfect conductor, $\lambda c$ is approximately 1.7 times d. The cross sectional area of the core may be circular, elliptical, oval, conical, rectangular, triangular, polyhedral, or in any other shape. Although uniform cross sectional area is generally preferred, the cross sectional area may vary at any given depth of the guide if desired.

The optical performance of the ZMW can be enhanced by incorporation within a micromirror structure on the substrate. The incorporation of micromirrors and other methods of improving optical performance in multiplex systems are describe in copending U.S. patent application Ser. No. 12/567,526, filed Sep. 25, 2009.

In the context of chemical or biochemical analyses within ZMWs as well as other optical confinements, it is generally desirable to ensure that the reactions of interest are taking place within the optically interrogated portions of the confinement, at a minimum, and preferably such that only the reactions of a single molecule is occurring within an interrogated portion of an individual confinement. A number of methods may generally be used to provide individual molecules within the observation volume. A variety of these are described in co-pending U.S. patent application Ser. No. 11/240,662, filed Sep. 30, 2005, incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these.

Base Calling and Sequence Determination

Figure 12:
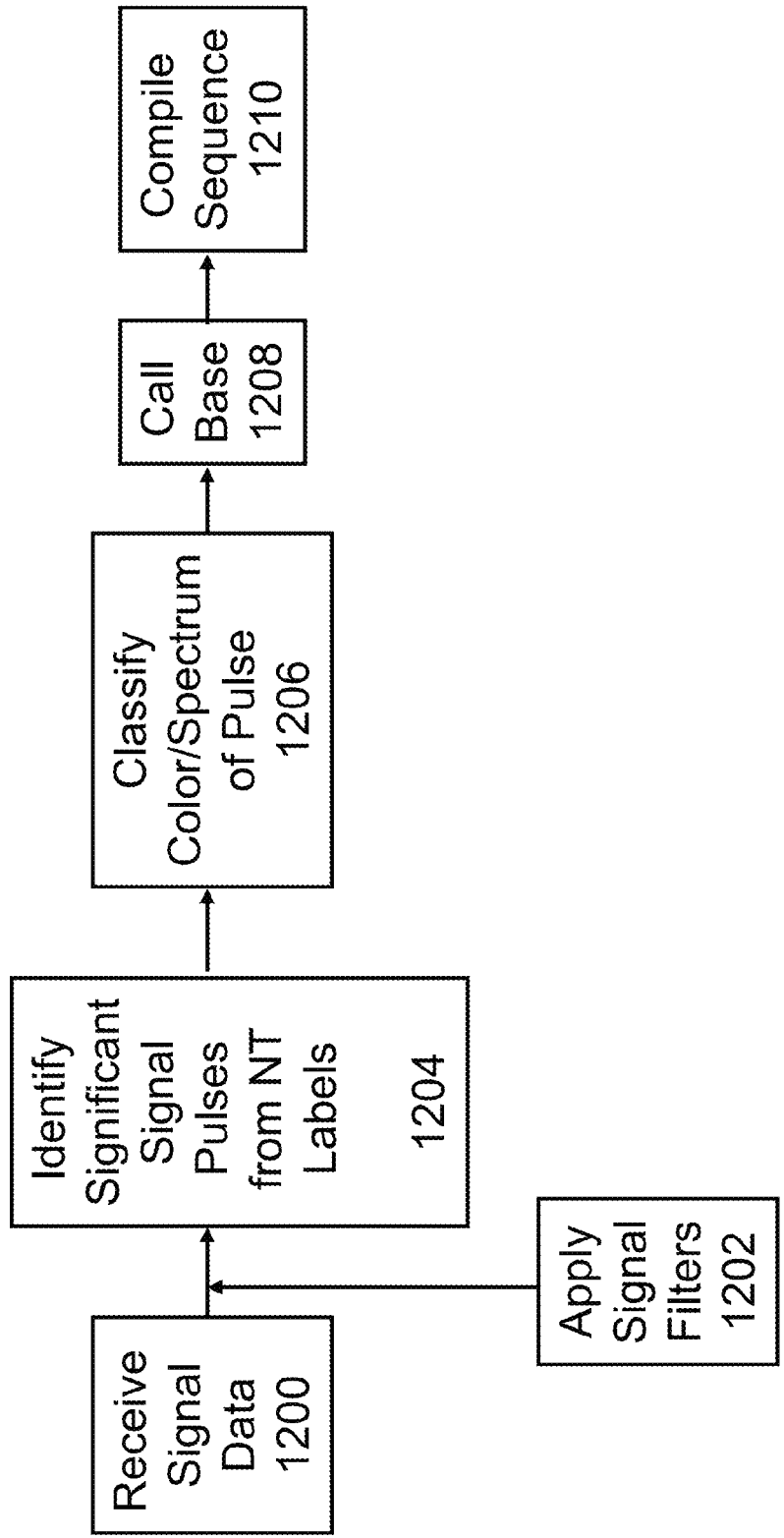
FIG. 12 shows a flow chart for an embodiment of a process for obtaining a nucleic acid sequence from signal data.

The systems and methods of the inventions can result in improved sequence determination and improved base calling by monitoring the signal from nucleotide analogs labeled on their 3' hydroxyl groups, and in some cases monitoring both the signal from the 3' hydroxyl leaving group and polyphosphate label. A general flow chart illustrating an embodiment of a base calling and sequence determination process using such signal data is provided in FIG. 12. In general, signal data is received by the processor at step 1200. The information received by the processor can come directly from the detection optics, or the signal from the detection optics can be treated by other processors before being received by the processor at step 1200. A number of initial calibrations operations may be applied at step 1202. Some of these initial calibration steps may be performed just once at the beginning of a run or on a more continuous basis during the run. These initial calibration steps can include such things as centroid determination, alignment, gridding, drift correction, initial background subtraction, noise parameter adjustment, frame-rate adjustment, etc. Some of these initial calibration steps, such as binning, may involve communication from the processor back to the detector/camera, as discussed further below.

Generally, some type of spectral trace determination/spectral trace extraction/spectral filters are applied to the initial signal data at step 1202. Some or all of this filter step may optionally be carried out at a later point in the process, e.g., after the pulse identification step 1204. The spectral trace extraction/spectral filters may include a number of noise reduction and other filters as set forth elsewhere herein. Spectral trace determination is performed at this stage for many of the example systems discussed herein because the initial signal data received are the light levels, or photon counts, captured by a series of adjacent pixel detectors. For example, in one example system, 14 pixels (or intensity levels) from 14 positions are captured for an individual wave-guide at each frame. Light of different frequencies or spectrum will fall on more than one of the 14 positions and there is generally some overlap and possibly substantial overlap. According to specific embodiments of the invention, spectral trace extraction may be performed using various analysis, as discussed below, that provide the highest signal-to-noise ratio for each spectral trace.

As an alternative to a spectral trace determination, methods of the invention may also analyze a single signal derived from the intensity levels at the multiple pixel positions (this may be referred to as a summed spectral signal or a gray-scale spectral signal or an intensity level signal). In many situations, it has been found that spectral extraction, however, provides better SNR and therefore pulse detection when extracted spectral traces are analyzed for pulses somewhat separately. In further embodiments, a method according to the invention may analyze the multiple captured pixel data using a statistical model such as a Hidden Markov Model. In present systems, however, determining multiple (e.g., four) spectral traces from the initial signal data has proven a preferred method.

Whether the signal from the labels on the nucleotides or the label or labels on the polymerase can be categorized as a significant signal pulse or event is determined at step 1204. In some example systems, because of the small number of photons available for detection and because of the speed of detection, various statistical analysis techniques may be performed in determining whether a significant pulse has been detected.

If the signal is identified as a significant pulse or signal event at step 1204, a further optional spectral profile comparison may be performed to verify the spectral assignment. This spectral profile comparison is optional in embodiments where spectral traces are determined prior to or during pulse identification. Once a color is assigned to a given incorporation signal, that assignment is used to call either the base incorporated, or its complement in the template sequence, at step 1208. In order to make this determination, the signals from the channel corresponding to the label on the enzyme which is sensitive to enzyme conformation is used to assess whether a pulse from a nucleotide label corresponds to an incorporation event. The compilation of called bases is then subjected to additional processing at step 1210, to provide linear sequence information, e.g., the successive sequence of nucleotides in the template sequence, assemble sequence fragments into longer contigs, or the like.

As noted above, the signal data is input into the processing system, e.g., an appropriately programmed computer or other processor. Signal data may input directly from a detection system, e.g., for real time signal processing, or it may be input from a signal data storage file or database. In some cases, e.g., where one is seeking immediate feedback on the performance of the detection system, adjusting detection or other experimental parameters, real-time signal processing will be employed. In some embodiments, signal data is stored from the detection system in an appropriate file or database and is subject to processing in post reaction or non-real time fashion.

The signal data used in conjunction with the present invention may be in a variety of forms. For example, the data may be numerical data representing intensity values for optical signals received at a given detector or detection point of an array based detector. Signal data may comprise image data from an imaging detector, such as a CCD, EMCCD, ICCD or CMOS sensor. In either event, signal data used according to specific embodiments of the invention generally includes both intensity level information and spectral information. In the context of separate detector elements, such spectral information will generally includes identification of the location or position of the detector portion (e.g., a pixel) upon which an intensity is detected. In the context of image data, the spectral image data will typically be the data derived from the image data that correlates with the calibrated spectral image data for the imaging system and detector when the system includes spectral resolution of overall signals. The spectral data may be obtained from the image data that is extracted from the detector, or alternatively, the derivation of spectral data may occur on the detector such that spectral data will be extracted from the detector.

For the sequencing methods described above, there will be a certain amount of optical signal that is detected by the detection system that is not the result of a signal from an incorporation event. Such signal will represent "noise" in the system, and may derive from a number of sources that may be internal to the monitored reaction, internal to the detection system and/or external to all of the above. Examples of noise internal to the reaction being monitored includes, e.g.: presence of fluorescent labels that are not associated with a detection event, e.g., liberated labels, labels associated with unincorporated bases in diffused in solution, bases associated with the complex but not incorporated; presence of multiple complexes in an individual observation volume or region; non-specific adsorption of dyes or nucleotides to the substrate or enzyme complex within an observation volume; contaminated nucleotide analogs, e.g., contaminated with other fluorescent components; other reaction components that may be weakly fluorescent; spectrally shifting dye components, e.g., as a result of reaction conditions; and the like. The use of information from the label on the polymerase sensitive to enzyme conformation provides a way of reducing or eliminating sources of noise, thereby improving the signal to noise of the system, and improving the quality of the base calls and associated sequence determination.

Sources of noise internal to the detection system, but outside of the reaction mixture can include, e.g., reflected excitation radiation that bleeds through the filtering optics; scattered excitation or fluorescent radiation from the substrate or any of the optical components; spatial cross-talk of adjacent signal sources; auto-fluorescence of any or all of the optical components of the system; read noise from the detector, e.g., CCDs, gain register noise, e.g., for EMCCD cameras, and the like. Other system derived noise contributions can come from data processing issues, such as background correction errors, focus drift errors, autofocus errors, pulse frequency resolution, alignment errors, and the like. Still other noise contributions can derive from sources outside of the overall system, including ambient light interference, dust, and the like.

These noise components contribute to the background photons underlying any signal pulses that may be associated with an incorporation event. As such, the noise level will typically form the limit against which any signal pulses may be determined to be statistically significant.

Identification of noise contribution to overall signal data may be carried out by a number of methods, including, for example, signal monitoring in the absence of the reaction of interest, where any signal data is determined to be irrelevant. Alternatively, and preferably, a baseline signal is estimated and subtracted from the signal data that is produced by the system, so that the noise measurement is made upon and contemporaneously with the measurements on the reaction of interest. Generation and application of the baseline may be carried out by a number of means, which are described in greater detail below.

In accordance with the present invention, signal processing methods distinguish between noise, as broadly applied to all non-significant pulse based signal events, and significant signal pulses that may, with a reasonable degree of confidence, be considered to be associated with, and thus can be tentatively identified as, an incorporation event. In the context of the present invention, a signal event is first classified as to whether it constitutes a significant signal pulse based upon whether such signal event meets any of a number of different pulse criteria. Once identified or classified as a significant pulse, the signal pulse may be further assessed to determine whether the signal pulse constitutes an incorporation event and may be called as a particular incorporated base. As will be appreciated, the basis for calling a particular signal event as a significant pulse, and ultimately as an incorporation event, will be subject to a certain amount of error, based upon a variety of parameters as generally set forth herein. As such, it will be appreciated that the aspects of the invention that involve classification of signal data as a pulse, and ultimately as an incorporation event or an identified base, are subject to the same or similar errors, and such nomenclature is used for purposes of discussion and as an indication that it is expected with a certain degree of confidence that the base called is the correct base in the sequence, and not as an indication of absolute certainty that the base called is actually the base in a given position in a given sequence.

One such signal pulse criterion is the ratio of the signals associated with the signal event in question to the level of all background noise ("signal to noise ratio" or "SNR"), which provides a measure of the confidence or statistical significance with which one can classify a signal event as a significant signal pulse. In distinguishing a significant pulse signal from systematic or other noise components, the signal generally must exceed a signal threshold level in one or more of a number of metrics, including for example, signal intensity, signal duration, temporal signal pulse shape, pulse spacing, and pulse spectral characteristics.

By way of a simplified example, signal data may be input into the processing system. If the signal data exceeds a signal threshold value in one or more of signal intensity and signal duration, it may be deemed a significant pulse signal. Similarly, if additional metrics are employed as thresholds, the signal may be compared against such metrics in identifying a particular signal event as a significant pulse. As will be appreciated, this comparison will typically involve at least one of the foregoing metrics, and preferably at least two such thresholds, and in many cases three or all four of the foregoing thresholds in identifying significant pulses.

Signal threshold values, whether in terms of signal intensity, signal duration, pulse shape, spacing or pulse spectral characteristics, or a combination of these, will generally be determined based upon expected signal profiles from prior experimental data, although in some cases, such thresholds may be identified from a percentage of overall signal data, where statistical evaluation indicates that such thresholding is appropriate. In particular, in some cases, a threshold signal intensity and/or signal duration may be set to exclude all but a certain fraction or percentage of the overall signal data, allowing a real-time setting of a threshold. Again, however, identification of the threshold level, in terms of percentage or absolute signal values, will generally correlate with previous experimental results. In alternative aspects, the signal thresholds may be determined in the context of a given evaluation. In particular, for example, a pulse intensity threshold may be based upon an absolute signal intensity, but such threshold would not take into account variations in signal background levels, e.g., through reagent diffusion, that might impact the threshold used, particularly in cases where the signal is relatively weak compared to the background level. As such, in certain aspects, the methods of the invention determine the background fluorescence of the particular reaction in question, including, in particular, the contribution of freely diffusing dyes or dye labeled analogs into a zero mode waveguide, and set the signal threshold above that actual background by the desired level, e.g., as a ratio of pulse intensity to background fluorophore diffusion, or by statistical methods, e.g., 5 sigma, or the like. By correcting for the actual reaction background, such as fluorophore diffusion background, the threshold is automatically calibrated against influences of variations in dye concentration, laser power, or the like. By reaction background is meant the level of background signal specifically associated with the reaction of interest and that would be expected to vary depending upon reaction conditions, as opposed to systemic contributions to background, e.g., autofluorescence of system or substrate components, laser bleedthrough, or the like.

In particularly preferred aspects that rely upon real-time detection of incorporation events, identification of a significant signal pulse may rely upon a signal profile that traverses thresholds in both signal intensity and signal duration. For example, when a signal is detected that crosses a lower intensity threshold in an increasing direction, ensuing signal data from the same set of detection elements, e.g., pixels, are monitored until the signal intensity crosses the same or a different intensity threshold in the decreasing direction. Once a peak of appropriate intensity is detected, the duration of the period during which it exceeded the intensity threshold or thresholds is compared against a duration threshold. Where a peak comprises a sufficiently intense signal of sufficient duration, it is called as a significant signal pulse.

In addition to, or as an alternative to using the intensity and duration thresholds, pulse classification may employ a number of other signal parameters in classifying pulses as significant. Such signal parameters include, e.g., pulse shape, spectral profile of the signal, e.g., pulse spectral centroid, pulse height, pulse diffusion ratio, pulse spacing, total signal levels, and the like.

Either following or prior to identification of a significant signal pulse, signal data may be correlated to a particular signal type. In the context of the optical detection schemes used in conjunction with the invention, this typically denotes a particular spectral profile of the signal giving rise to the signal data. In particular, the optical detection systems used in conjunction with the methods and processes of the invention are generally configured to receive optical signals that have distinguishable spectral profiles, where each spectrally distinguishable signal profile may generally be correlated to a different reaction event. In the case of nucleic acid sequencing, for example, each spectrally distinguishable signal may be correlated or indicative of a specific nucleotide incorporated or present at a given position of a nucleic acid sequence. Consequently, the detection systems include optical trains that receive such signals and separate the signals based upon their spectra. The different signals are then directed to different detectors, to different locations on a single array based detector, or are differentially imaged upon the same imaging detector (See, e.g., U.S. Patent Publication No. 2007/0036511, which is incorporated herein by reference in its entirety for all purposes).

In the case of systems that employ different detectors for different signal spectra, assignment of a signal type (for ease of discussion, referred to hereafter as "color classification" or "spectral classification") to a given signal is a matter of correlating the signal pulse with the detector from which the data derived. In particular, where each separated signal component is detected by a discrete detector, a signal's detection by that detector is indicative of the signal classifying as the requisite color.

In preferred aspects, however, the detection systems used in conjunction with the invention utilize an imaging detector upon which all or at least several of the different spectral components of the overall signal are imaged in a manner that allows distinction between different spectral components. Thus, multiple signal components are directed to the same overall detector, but may be incident upon wholly or partly different regions of the detector, e.g., imaged upon different sets of pixels in an imaging detector, and give rise to distinguishable spectral images (and associated image data). As used herein, spectra or spectral image generally indicates a pixel image or frame (optionally data reduced to one dimension) that has multiple intensities caused by the spectral spread of an optical signal received from a reaction location.

In its simplest form, it will be understood that assignment of color to a signal event incident upon a group of contiguous detection elements or pixels in the detector would be accomplished in a similar fashion as that set forth for separate detectors. In particular, the position of the group of pixels upon which the signal was imaged, and from which the signal data is derived, is indicative of the color of the signal component. In particularly preferred aspects, however, spatial separation of the signal components may not be perfect, such that signals of differing colors are imaged on overlapping sets of pixels. As such, signal identification will generally be based upon the aggregate identity of multiple pixels (or overall image of the signal component) upon which a signal was incident.

Once a particular signal is identified as a significant pulse and is assigned a particular spectrum, the spectrally assigned pulse may be further assessed to determine whether the pulse can be called an incorporation event and, as a result, call the base incorporated in the nascent strand, or its complement in the template sequence. Signals from the 3'-hydroxyl leaving group label and the polyphosphate label are used to identify which base should be called. As described above. By using two labels per nucleotide analog, either interacting or non-interacting, a set of characteristic signals are produced which can be correlated with high confidence to an incorporation event.

In addition, calling of bases from color assigned pulse data will typically employ tests that again identify the confidence level with which a base is called. Typically, such tests will take into account the data environment in which a signal was received, including a number of the same data parameters used in identifying significant pulses, etc. For example, such tests may include considerations of background signal levels, adjacent pulse signal parameters (spacing, intensity, duration, etc.), spectral image resolution, and a variety of other parameters. Such data may be used to assign a score to a given base call for a color assigned signal pulse, where such scores are correlative of a probability that the base called is incorrect, e.g., 1 in 100 (99% accurate), 1 in 1000 (99.9% accurate), 1 in 10,000 (99.99% accurate), 1 in 100,000 (99.999% accurate), or even greater. Similar to PHRED or similar type scoring for chromatographically derived sequence data, such scores may be used to provide an indication of accuracy for sequencing data and/or filter out sequence information of insufficient accuracy.

Once a base is called with sufficient accuracy, subsequent bases called in the same sequencing run, and in the same primer extension reaction, may then be appended to each previously called base to provide a sequence of bases in the overall sequence of the template or nascent strand. Iterative processing and further data processing can be used to fill in any blanks, correct any erroneously called bases, or the like for a given sequence.

Figure 13:
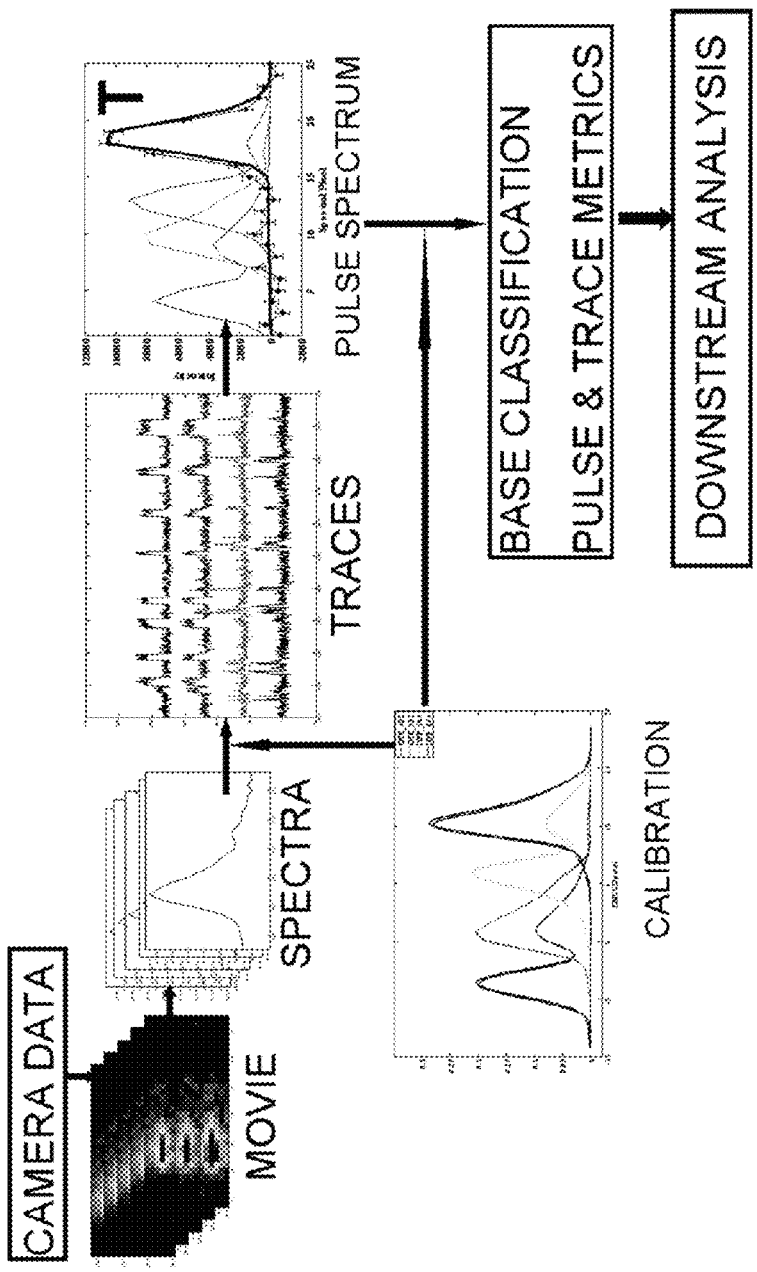
FIG. 13 shows a representation of a process of converting optical data into a nucleic acid sequence.

Analysis of sequencing-by-incorporation-reactions on an array of reaction locations according to specific embodiments of the invention is also illustrated graphically in FIG. 13. In this summary figure, data captured by a camera is represented as a movie, which is also a time sequence of spectra. Spectral calibration templates are used to extract traces from the spectra. Pulses identifies in the traces are then used to return to the spectra data and from that data produce a temporally averaged pulse spectrum for each pulse, such pulse spectra will include spectra for events relating to enzyme conformational changes. The spectral calibration templates are then also used to classify pulse spectrum to a particular base. Base classifications and pulse and trace metrics are then stored or passed to other logic for further analysis. The downstream analysis will include using the information from enzyme conformational changes to assist in the determination of incorporation events for base calling. Further base calling and sequence determination methods for use in the invention are described in copending U.S. patent application Ser. No. 12/134,186, filed Jun. 5, 2008.

It is to be understood that the above description is intended to be illustrative and not restrictive. It readily should be apparent to one skilled in the art that various embodiments and- modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

What is claimed is:

1. A method of determining the nucleotide sequence of a target nucleic acid sequence, comprising the steps of:
   (a) providing a reaction complex comprising a template nucleic acid comprising a target nucleic acid sequence, a primer nucleic acid comprising a sequence which is complementary to a region of the template nucleic acid, and a polymerase enzyme or an enzyme complex, which comprises 5' to 3' polymerization activity and 3' to 5' exonuclease activity;
   (b) contacting the reaction complex with a plurality of nucleotide analogs, wherein at least one individual nucleotide analog of said plurality comprises at least one base-pairing moiety, at least one residue that can be removed by an exonuclease activity, and at least one label moiety comprising a photo-detectable label that is indicative of the identity of the base-pairing moiety;
   (c) allowing the enzyme or enzyme complex to incorporate a nucleotide analog in a template-dependent manner into a nascent strand via the enzyme's or enzyme complex's 5' to 3' polymerization activity, whereby the label moiety of the nucleotide analog is coupled to the nascent strand;
   (d) detecting the photo-detectable label of the incorporated nucleotide analog while the label moiety is coupled to the nascent strand;
   (e) after step (d), allowing the enzyme or enzyme complex to remove the label moiety of the incorporated nucleotide analog from the nascent strand via the enzyme's or enzyme complex's 3' to 5' exonuclease activity; and
   (f) repeating steps (c)-(e) to determine the sequence of the target nucleic acid sequence.

2. The method of claim 1, wherein the photo-detectable label is a fluorophore.

3. The method of claim 2, wherein the nucleotide analog further comprises at least one fluorescence quenching moiety, and wherein the fluorescence quenching moiety is removed from the nucleotide analog upon incorporation of the nucleotide analog via the enzyme's or enzyme complex's 5' to 3' polymerization activity into the nascent strand.

4. The method of claim 1, wherein the at least one base-pairing moiety, having a 5' end and a 3' end, comprises one or more nucleotide residues that each comprises a base that is able to base pair with a corresponding base of the target nucleic acid sequence in an active site of the reaction complex.

5. The method of claim 4, wherein the 3' end of the base-pairing moiety is connected to the label moiety via a phosphate linkage.

6. The method of claim 1 wherein at least one of said plurality of nucleotide analogs is chosen from compounds having Formula IV:

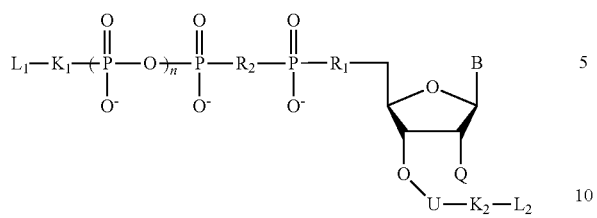

Formula IV wherein B is a nucleobase; Q is H, OH, SH, or NHR; $R_1$ is selected from O and S; $R_2$ is selected from O, NH, NR, S, $CH_2$, CRR', $CH_2CH_2$, CRR'CRR', C(O), CRNHR', where R and R' are independently selected from H, F, Cl, OH, NH2, methyl, ethyl, propyl, $C_2$-$C_6$ alkyl, $C_2$-$C_6$ alkenyl, $C_2$-$C_6$ alkynyl, aryl, heterocycle, 4-pyridine, and 1-imidazone; U is a single bond,

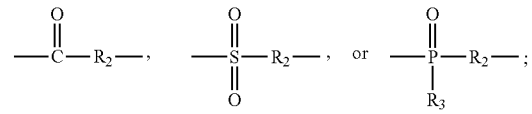

$R_3$ is selected from —OR, —SR, —NRR', or —$CH_2R$; $K_1$ and $K_2$ are linker moieties; $L_1$ and $L_2$ are detectable labels; and n is from 0 to 6 wherein $K_2$ comprises a structure of Formula III:

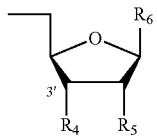

Formula III wherein $R_4$ and $R_5$, are independently selected from a bond to $L_2$, H, OH, $OR_7$, $SR_7$ or $NHR_7$; $R_7$ is H, methyl or a $C_2$-$C_6$ alkyl group; and $R_6$ is either a bond to $L_2$, a nucleobase, or an aryl, heteroaryl, or $C_1$-$C_6$ aliphatic moiety.

7. The composition of claim 6 wherein $L_1$ and $L_2$ are members of a donor-quencher or a FRET pair.

8. The composition of claim 6 wherein B comprises A, T, G, C, U or I.

9. A method of determining the nucleotide sequence of a target nucleic acid sequence, comprising the steps of:
(a) providing a reaction complex comprising a template nucleic acid comprising a target nucleic acid sequence, a primer nucleic acid comprising a sequence which is complementary to a region of the template nucleic acid, and a polymerase enzyme or an enzyme complex, which comprises 5' to 3' polymerization activity and 3' to 5' exonuclease activity;
(b) contacting the reaction complex with a plurality of nucleotide analogs;
(c) allowing the enzyme or enzyme complex to incorporate a nucleotide analog in a template-dependent manner into a nascent strand via 5' to 3' polymerization activity of the enzyme or enzyme complex;
(d) detecting a photo-detectable label moiety on the incorporated nucleotide analog while the label moiety is coupled to the nascent strand;
(e) after step (d), allowing the enzyme or enzyme complex to remove the label moiety of the incorporated nucleotide analog from the nascent strand via 3' to 5' exonuclease activity of the enzyme or enzyme complex; and
(f) repeating steps (c)-(e) to determine the sequence of the target nucleic acid sequence,
wherein at least one of the plurality of nucleotide analogs is chosen from compounds having Formula IV:

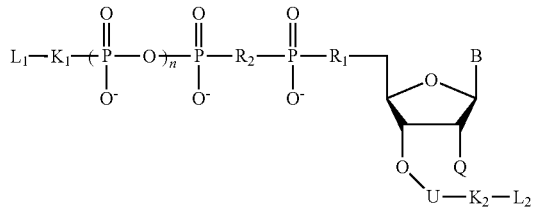

Formula IV wherein B is a nucleobase; Q is H, OH, SH, or NHR; $R_1$ is selected from O and S; $R_2$ is selected from O, NH, NR, S, $CH_2$, CRR', CH2CH2, CRR'CRR', C(O), CRNHR', where R and R' are independently selected from H, F, Cl, OH, NH2, methyl, ethyl, propyl, $C_2$-$C_6$ alkyl, $C_2$-$C_6$ alkenyl, $C_2$-$C_6$ alkynyl, aryl, heterocycle, 4-pyridine, and 1-imidazone; U is a single bond, $R_3$ is selected from —OR, —SR, —NRR', or —$CH_2R$; $K_1$ and $K_2$ are linker moieties; $L_1$ and $L_2$ are detectable labels; and n is from 0 to 6 wherein $K_2$ comprises a structure of Formula III:

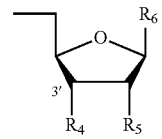

Formula III wherein $R_4$ and $R_5$, are independently selected from a bond to $L_2$, H, OH, $OR_7$, $SR_7$ or $NHR_7$; $R_7$ is H, methyl or a $C_2$-$C_6$ alkyl group; and $R_6$ is either a bond to $L_2$, a nucleobase, or an aryl, heteroaryl, or $C_1$-$C_6$ aliphatic moiety.

10. The composition of claim 9 wherein $L_1$ and $L_2$ are members of a donor-quencher or a FRET pair.

11. The composition of claim 9 wherein B comprises A, T, G, C, U or I.

12. The method of claim 1, wherein the plurality of nucleotide analogs comprises at least four types of nucleotide analogs, each type comprising a unique base-pairing moiety and a unique fluorophore that is distinguishable from the fluorophores of the other types of nucleotide analogs of said plurality.

13. The method of claim 12, wherein the plurality of nucleotide analogs further comprises a nucleotide analog having a fluorescence quenching moiety that is removed from the nucleotide analog upon incorporation of the nucleotide analog into the nascent strand.

14. A method of determining a nucleotide base incorporated by a polymerase enzyme or enzyme complex in a nucleic add polymerization reaction, the method comprising the steps of:
   (a) conducting a nucleic acid polymerization reaction that utilizes both 5' to 3' polymerization activity and 3' to 5' exonuclease activity of a polymerase enzyme or enzyme complex, and that results in production of a nascent strand in a template-dependent manner, wherein said reaction is conducted in the presence of:
      (i) a template nucleic acid comprising a target nucleic acid sequence,
      (ii) a primer nucleic acid comprising a sequence which is complementary to a region of the template nucleic acid,
      (iii) a polymerase enzyme or an enzyme complex comprising 5' to 3' polymerization activity and 3' to 5' exonuclease activity,
      (iv) a plurality of nucleotide analogs, wherein at least one nucleotide analog of said plurality comprises at least one base-pairing moiety, at least one residue that can be cleaved by an exonuclease activity, and at least one label moiety, said label moiety comprising a photo-detectable label,
      wherein the label moiety of an individual nucleotide analog becomes incorporated into the nascent strand;
   (b) detecting the photo-detectable label while the label moiety is coupled to the nascent strand, wherein said label is indicative of the identity of the base or bases present in the nucleotide analog incorporated by the enzyme or enzyme complex into the nascent strand; and
   (c) after step (b), allowing the 3' to 5' exonuclease activity of the enzyme or enzyme complex to remove the labeled moiety from the nascent strand.

15. The method of claim 14, wherein said detecting step is performed during each successive nucleotide incorporation event after the photo-detectable label of the nucleotide analog incorporated in the previous incorporation event is removed via the 3' to 5' exonuclease activity of the enzyme or enzyme complex.

16. The method of claim 1 wherein the at least one residue that can be removed by an exonuclease activity comprises a nucleotide.

17. The method of claim 1 wherein the at least one residue that can be removed by an exonuclease activity comprises the structure:

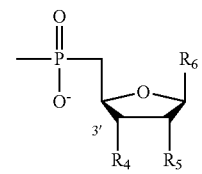

wherein $R_4$ and $R_5$, are independently selected from a bond to $L_2$, H, OH, $OR_7$, $SR_7$ or $NHR_7$; $R_7$ is H, methyl or a C2-C6 alkyl group; and $R_6$ is either a bond to $L_2$, a nucleobase, or an aryl, heteroaryl, or C1-C6 aliphatic moiety, wherein L2 is a detectable label.

18. The method of claim 17 wherein $R_6$ is a substituted or unsubstituted 5- or 6-membered unsaturated ring containing one, two, three, or four independently selected heteroatoms, independently selected from oxygen, nitrogen, and sulfur.

19. The method of claim 17 wherein $R_6$ is a substituted or unsubstituted, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, or benzothienyl.

* * * * *